(12) United States Patent
Richter et al.

(10) Patent No.: US 7,645,782 B2
(45) Date of Patent: *Jan. 12, 2010

(54) THIA-EPOTHILONE DERIVATIVES FOR THE TREATMENT OF CANCER

(75) Inventors: Wolfgang Richter, Martinsried (DE); Lutz Weber, Germering (DE)

(73) Assignees: Wolfgang Richter, Munich (DE); Morphochem Aktiengesellschaft fur Kombinatorische Chemie, Braunschweig (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/535,474

(22) PCT Filed: Nov. 28, 2003

(86) PCT No.: PCT/EP03/13412

§ 371 (c)(1),
(2), (4) Date: May 17, 2005

(87) PCT Pub. No.: WO2004/048372

PCT Pub. Date: Jun. 10, 2004

(65) Prior Publication Data

US 2006/0128966 A1    Jun. 15, 2006

(30) Foreign Application Priority Data

Nov. 28, 2002 (DE) ............................. 102 55 681
Jun. 18, 2003 (DE) ............................. 103 27 472

(51) Int. Cl.
| | |
|---|---|
| A61K 31/427 | (2006.01) |
| A61K 31/428 | (2006.01) |
| A61K 31/39 | (2006.01) |
| C07D 277/64 | (2006.01) |
| C07D 277/30 | (2006.01) |
| C07D 327/02 | (2006.01) |

(52) U.S. Cl. ................. 514/365; 514/367; 514/431; 514/450; 548/180; 548/204; 549/10; 549/266

(58) Field of Classification Search ............... 514/365, 514/367, 431, 450; 548/180, 204; 549/10, 549/266

See application file for complete search history.

(56) References Cited

U.S. PATENT DOCUMENTS 7,056,942 B2 * 6/2006 Hildesheim et al. ......... 514/411
2006/0004065 A1 * 1/2006 Hoefle et al. ................ 514/365

FOREIGN PATENT DOCUMENTS

WO    WO 2004007492 A1 * 1/2004

OTHER PUBLICATIONS

Nicolaou et al. "Chemical Biology of Epothilones" Angew. Chem. Int. Ed. 1998, vol. 37, pp. 2014-2045.*
Florsheimer et al. "Epothilones and their analogues—a new class of promising microtubule inhibitors" Expert Opin. Ther. Patents 2001, vol. 11, Iss 6, pp. 951-968.*
Patani et al. "Bioisosterism: A Rational Approach in Drug Design" Chem. Rev. 1996, vol. 96, pp. 3147-3176.*
Feyen, F.,et al. "Design and Synthesis of 12-Aza-Epothilones (Azathilones)-"Non-Natural" Natural Products with Potent Anticancer Activity", *Angew. Chem. Int. Ed.* 45, 1-6 (2006).
Altmann, K.,"Epothilone B and its Analogs-A New Family of Anticancer Agents" *Mini Reviews in Medicial Chemistry*, vol. 3, No. 2 150-158 (2003).
White, J. et al."Total Synthesis of Epothilone B, Epothilone D, and cis- and Trans-9, 10- Dehydroepothilone D", *J.Am. Chem. Soc.*, vol. 123, No. 23, 5407-5413 (2001).
Hofle, G. ,et al. "Epothilone, a Myxobacterial Metabolite with Promising Antitumor Activity." *Anticancer Agents from Natural Products* Cragg et al. eds.Taylor & Francis, Boca Raton, FL 413-449 (2005).

* cited by examiner

*Primary Examiner*—Rei-Tsang Shiao
*Assistant Examiner*—Joseph R Kosack
(74) *Attorney, Agent, or Firm*—Edwards Angell Palmer & Dodge LLP; Peter F. Corless; Nicholas J. DiCeglie, Jr.

(57) ABSTRACT

The present invention relates to new Macrocycles of formula (I) and their use for the treatment of cancer.

10 Claims, No Drawings

THIA-EPOTHILONE DERIVATIVES FOR THE TREATMENT OF CANCER

Epothilones (DE4138042) are polyketide natural products that inhibit cancer cells by a mechanism similar to paclitaxel, and also are effective against paclitaxel-resistant tumours. Several epothilone derivatives are currently undergoing clinical trials for the cure of several cancers (Nicolaou et al. Angew. Chem. Int. Ed. 1998, 37, 2014-2045; Flörsheimer et al. Expert Opin. Ther. Patents 2001, 11, 951-968).

The object of the present invention is to provide new epothilone-like compounds with improved pharmacological properties.

The present invention provides compounds of Formula (I):

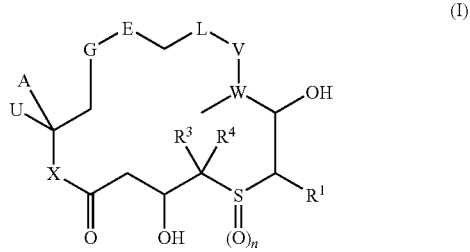

wherein
A is a heteroalkyl-, heterocycloalkyl-, heteroalkylcycloalkyl-, heteroaryl- or heteroarylalkyl-group,
U is hydrogen, halogen, an alkyl, heteroalkyl-, heterocycloalkyl-, heteroalkylcycloalkyl-, heteroaryl- or heteroarylalkyl-group,
G-E is selected from the following groups,

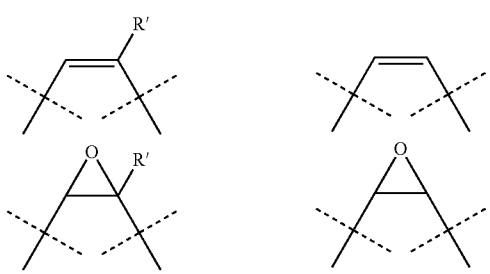

wherein R' is F or a $C_1$-$C_3$ alkyl group or G-E is part of an optionally substituted phenyl ring,
$R^1$ is a $C_1$-$C_4$-alkyl-, a $C_1$-$C_4$-alkenyl-, a $C_1$-$C_4$-alkynyl- or a $C_3$-$C_4$-cycloalkyl-group,
L-V—W is a group of formula CH=CH—CH, $CH_2$—$CH_2$—CH or $CH_2$—CH=C, wherein the double bonds may be cis or trans isomers,
n is 0 or 2,
X is oxygen or a group of the formula $NR^2$, wherein $R^2$ is hydrogen, an alkyl-, alkenyl-, alkynyl-, heteroalkyl-, aryl-, heteroaryl-, cycloalkyl-, alkylcycloalkyl-, heteroalkylcycloalkyl-, heterocycloalkyl-, aralkyl- or heteroarylalkyl-group and
$R^3$ and $R^4$ independently from each other represent hydrogen, $C_1$-$C_4$-alkyl or together are part of a cycloalkyl group with 3 or 4 ring atoms, or a pharmacologically acceptable salt, solvate, hydrate or formulation thereof.

It should be appreciated that certain compounds of Formula (I) may have tautomeric forms from which only one might be specifically mentioned or depicted in the following description, different geometrical isomers (which are usually denoted as cis/trans isomers or more generally as (E) and (Z) isomers) or different optical isomers as a result of one or more asymmetric or chiral carbon atoms (which are usually nomenclatured under the Cahn-Ingold-Prelog or R/S system). Further, some compounds may display polymorphism. All these tautomeric forms, geometrical or optical isomers (as well as racemates and diastereomers) and polymorphous forms are included in the invention.

The term alkyl refers to a saturated straight or branched chain alkyl group, containing from one or two to ten carbon atoms, preferably from one or two to six carbon atoms, e.g. 1 or 2 to 4 carbon atoms, for example methyl, ethyl, propyl, iso-propyl, butyl, iso-butyl, tert.-butyl, n-hexyl, 2,2-dimethylbutyl or n-octyl groups.

The terms alkenyl and alkynyl refer to unsaturated straight or branched chain alkyl groups, containing from two to ten carbon atoms, preferably from two to six carbon atoms, e.g. 2 to 4 carbon atoms, for example ethenyl (vinyl), propenyl, iso-propenyl, butenyl, isoprenyl or hexa-2-enyl; ethynyl, propynyl or butynyl groups.

The terms alkyl, alkenyl and alkynyl moreover refer to groups, wherein one or more hydrogen atoms are replaced by halogen atoms such as fluorine or chlorine, for example trifluoromethyl or 1,1-Dichloroethyl groups.

The term heteroalkyl refers to an alkyl, alkenyl or alkynyl group as defined herein where one or more carbon atoms are replaced by an oxygen, nitrogen, phosphorous or sulphur atom, for example an alkoxy group containing from one to ten carbon atoms, preferably from one to six carbon atoms, e.g. 1 to 4 carbon atoms, such as methoxy, ethoxy, propoxy, iso-propoxy, butoxy or tert.-butoxy; a (1-4C)alkoxy(1-4C)alkyl group such as methoxymethyl, ethoxymethyl, 1-methoxyethyl, 1-ethoxyethyl, 2-methoxyethyl or 2-ethoxyethyl; or a cyano group; or a 2,3-dioxyethyl group. The term heteroalkyl furthermore refers to a group derived from a carboxylic acid or carboxylic acid amide containing from one to ten carbon atoms, preferably from one to six carbon atoms, e.g. 1 to 4 carbon atoms, and may, for example, be acyl containing from one to ten carbon atoms, preferably from one to six carbon atoms, e.g. 1 to 4 carbon atoms, such as acetyl, propionyl, butyryl or pivaloyl; acyloxy containing from one to ten carbon atoms, preferably from one to six carbon atoms, e.g. 1 to 4 carbon atoms such as acetyloxy, propionyloxy, butyryloxy or pivaloyloxy; carboxyalkyl containing from one to ten carbon atoms, preferably from one to six carbon atoms, e.g. 1 to 4 carbon atoms such as carboxymethyl, carboxyethyl, carboxypropyl, carboxybutyl, carboxyalkyl ester containing from one to ten carbon atoms, preferably from one to six carbon atoms, e.g. 1 to 4 carbon atoms, such as carboxyalkyl methyl ester, carboxyalkyl ethyl ester, carboxyalkyl propyl ester, carboxyalkyl isopropyl ester, carboxyalkyl butyl ester or carboxyalkyl tert.-butyl ester, carboxyalkyl amide or alkylcarbamoyl such as N-(1-4C)alkylcarbamoyl or N,N'-(1-4C) dialkylcarbamoyl) containing from one to ten carbon atoms, preferably from one to six carbon atoms, e.g. 1 to 4 carbon atoms such as N-methylcarbamoyl, N-ethylcarbamoyl, N-propylcarbamoyl, N,N'-dimethylcarbamoyl, N-ethyl-N-methylcarbamoyl or N,N'-dipropylcarbamoyl, alkoxycarbonyl containing from one to ten carbon atoms, preferably from one to six carbon atoms, e.g. 1 to 4 carbon atoms, such as methoxycarbonyl, ethoxy-carbonyl, propoxycarbonyl, iso-propoxycarbonyl, butoxy- or tert.-butoxycarbonyl or alkoxycarbonyloxy containing from one to ten carbon atoms, preferably from one to six carbon atoms, e.g. 1 to 4 carbon atoms such as methoxycarbonyloxy, ethoxycarbonyloxy, propoxycarbonyloxy, isopropoxycarbonyloxy, butoxycarbonyloxy, tert.-butoxycarbonyloxy.

The term cycloalkyl refers to a saturated or partially unsaturated cyclic group, having one or more rings, formed by three to 14 ring-carbon atoms, preferably by three, four, five or six to nine or ten ring-carbon atoms, for example cyclopropyl, cyclobutyl, cyclopentyl, cyclohexyl, tetralin, cyclopentenyl or cyclohex-2-enyl groups.

The term heterocycloalkyl refers to a cycloalkyl group as defined herein where one or more ring-carbon atoms are replaced by one or more oxygen, nitrogen, phosphorous or sulphur atoms. Specific examples for heterocyclalkyl are piperidino, morpholino, N-methyl-piperazino or N-phenyl-piperazino groups.

The term aryl refers to an aromatic cyclic group, having one or more rings, formed by five to 14 ring-carbon atoms preferably by five or six to nine or ten ring-carbon atoms, for example phenyl, indene, indenyl or naphthyl groups. Specific examples are a benzyl, tolyl, phenethyl, biphenyl, xylyl, cumyl, 2-, 3- or 4-methoxyphenyl, 2-, 3- or 4-ethoxyphenyl, 4-carboxyphenyl alkyl or a 4-hydroxyphenyl group.

The term heteroaryl refers to an aryl group as defined herein where one or more ring-carbon atoms are replaced by, an oxygen, nitrogen, phosphorous or sulphur atom, for example 4-pyridyl, 2-imidazolyl, 3-pyrazolyl, quinolinyl, isoquinolinyl, pyrrolyl, oxazolyl, isoxazolyl, thiazolyl, isothiazolyl, 1,2,3-triazolyl, 1,2,4-triazolyl, oxadiazolyl, thiadiazolyl, indolyl, indazolyl, tetrazolyl, pyrazinyl, pyridinyl, pyrimidinyl and pyridazinyl groups.

The terms aralkyl and heteroarylalkyl refer to groups that comprise both aryl or, respectively, heteroaryl as well as alkyl, alkenyl, alkinyl and/or heteroalkyl (for example alkoxy groups in case of aralkyloxy) and/or cycloalkyl and/or heterocycloalkyl ring systems as defined herein. Examples are the tetrahydroisoquinolinyl, benzyl, benzyloxy, 2- or 3-ethyl-indolyl or 4-methylpyridino groups.

The terms alkylcycloalkyl and heteroalkylcycloalkyl refer to groups that comprise both cycloalkyl or, respectively, heterocycloalkyl as well as alkyl, alkenyl, alkynyl and/or heteroalkyl (for example alkoxy groups in case of aralkyloxy) groups as defined herein.

Any alkyl, alkenyl, alkynyl, heteroalkyl, cycloalkyl, heterocycloalkyl, aryl, heteroaryl aralkyl or heteroarylalkyl groups as defined herein may be substituted with one or more halogen atoms, $NH_2$, SH, $NO_2$ or OH groups or unsubstituted alkyl, heteroalkyl, aryl, aralkyl, aralkyloxy, heteroaryl, cycloalkyl or heterocycloalkyl groups as defined herein.

The term "optionally substituted" refers to groups wherein one or more hydrogen atoms may be replaced a halogen atom, a $NH_2$, SH, $NO_2$ or OH group or by an unsubstituted alkyl, heteroalkyl, aryl, aralkyl, aralkyloxy, heteroaryl, cycloalkyl or heterocycloalkyl group as defined herein.

Preferred and/or advantageous embodiments of the invention are subject-matter of the subclaims.

Preferred are compounds of formula (I), wherein A is a group of the formula —$C(CH_3)$=$CHR^5$ or —CH=$CHR^5$, wherein $R^5$ is a heteroaryl- or a heteroarylalkyl group.

Further preferred are compounds of formula (I), wherein A is a group of formula (II) or (III):

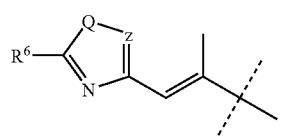
(II)

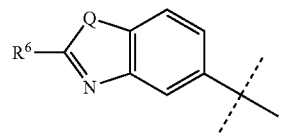
(III)

wherein Q is sulphur, oxygen or $NR^7$ (especially oxygen or sulphur), wherein $R^7$ is hydrogen, $C_1$-$C_4$ alkyl or $C_1$-$C_4$ heteroalkyl, z is Nitrogen or CH (especially CH) and $R^6$ is $OR^8$, $NHR^8$, $C_1$-$C_4$ alkyl, $C_1$-$C_4$ alkenyl, $C_1$-$C_4$ alkynyl or $C_1$-$C_6$ heteroalkyl (especially methyl, $CH_2OR^8$ or $CH_2NHR^8$), wherein $R^8$ is hydrogen, $C_1$-$C_4$ alkyl or $C_1$-$C_4$ heteroalkyl (especially hydrogen).

Moreover preferred are compounds of formula (I), wherein $R^2$ is hydrogen or $C_1$-$C_4$ alkyl.

Further preferred are compounds of formula (I), wherein X is oxygen or NH.

Moreover preferred are compounds of formula (I), wherein $R^1$ is methyl or ethyl (especially methyl).

Further preferred are compounds of formula (I), wherein $R^3$ and $R^4$ are methyl groups.

Moreover preferred are compounds of formula (I), wherein U is hydrogen, fluorine, methyl, trifluoromethyl or COOH (especially hydrogen).

Further preferred are compounds of formula (I), wherein the absolute stereochemistry is the same as in the natural occurring epothilones B and/or D.

Moreover preferred are compounds of formula (I), wherein R' is $CH_3$ or $CF_3$.

The present invention also relates to pharmacologically acceptable salts, or solvates and hydrates, respectively, and to compositions and formulations of compounds of Formula (I). The pharmaceutical compositions according to the present invention contain at least one compound of Formula (I) as the active agent and optionally carriers and/or diluents and/or adjuvants.

Examples of pharmacologically acceptable salts of sufficiently basic compounds of Formula (I) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleinic and salicylic acid. Further, a sufficiently acid compound of Formula (I) may form alkali or earth alkali metal salts, for example sodium, potassium, lithium, calcium or magnesium salts; ammonium salts; or organic base salts, for example methylamine, dimethylamine, trimethylamine, tri-ethylamine, ethylenediamine, ethanolamine, choline hydroxide, N-methyl-D-aminomethane (meglumin), piperidine, morpholine, tris-(2-hydroxyethyl)amine, lysine or arginine salts. Compounds of Formula (I) may be solvated, especially hydrated. The hydratisation can occur during the process of production or as a consequence of the hygroscopic nature of the initially water free compounds of Formula (I). The compounds of Formula (I) contain asymmetric C-atoms and may be present either as achiral compounds, mixtures of diastereomers, mixtures of enantiomers or as optically pure compounds.

The present invention also relates to pro-drugs (for a definition and examples see, e.g. R. B. Silverman, Medizinische Chemie, VCH Weinheim, 1995, Kapitel 8, S. 361ff) which are composed of a compound of Formula (I) and at least one pharmacologically acceptable protective group which will be cleaved off under physiological conditions, such as an alkoxy-, aralkyloxy-, acyl- or acyloxy group as defined herein, e.g. ethoxy, benzyloxy, acetyl or acetyloxy.

As mentioned above, therapeutically useful agents that contain compounds of Formula (I), their solvates, salts and formulations are also comprised in the scope of the present invention. Furthermore the use of compounds of formula (I) for the manufacture of medicaments for the treatment of cancer is also comprised in the scope of the present invention. In general, compounds of Formula (I) will be administered by using the known and acceptable modes known in the art, either alone or in combination with any other therapeutic agent. Such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containg the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatin, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use excipients as are e.g. water, alcohols, aqueous saline, aqueous dextrose, polyols, glycerin, vegetable, petroleum, animal or synthetic oils. For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilisation, e.g. UV stabilizers, emulsifiers, sweetener, aromatisers, salts to change the osmotic pressure, buffers, coating additives and antioxidants.

Combinations with other therapeutic agents may include other therapeutically useful agents, e.g. that are used to prevent or treat cancer.

For the prevention and/or treatment of cancer the dose of the biologically active compound may vary within broad limits and can be adjusted to the individual needs. In general a dose of 0.1 microgram to 100 milligram per kilogram body weight per day is appropriate, with a preferred dose of 10 micrograms to 25 milligrams/kilogram per day. In appropriate cases the dose may be also higher or lower than given above.

Compounds (IVa), (IVb), (Va) and (Vb) are key building blocks in the synthesis of compounds according to the present invention and are also included in the scope of the invention.

-continued

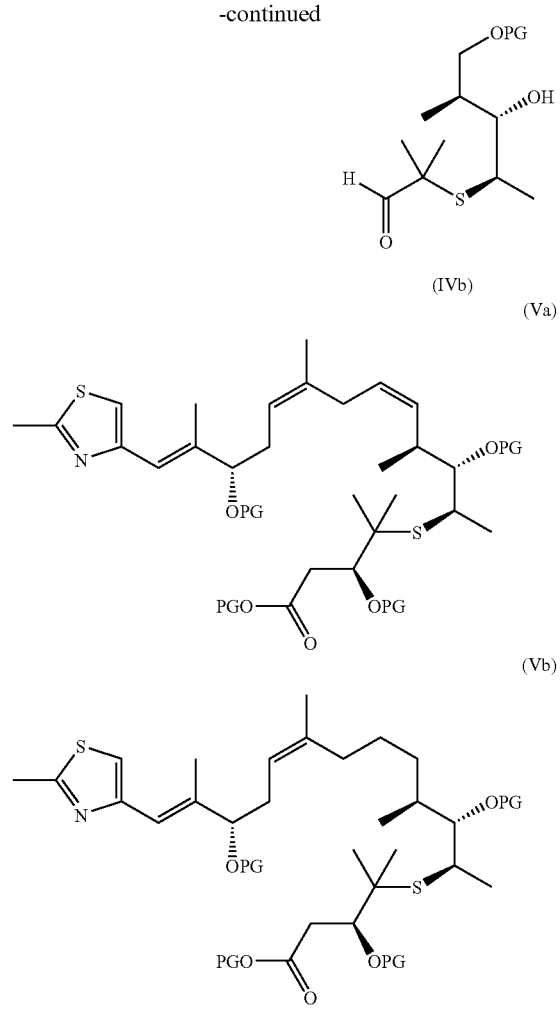

(IVb)

(Va)

(Vb)

Herein, the groups PG independently from each other represent hydrogen or protecting groups for alkohols (P. J. Kocienski, Protecting Groups, Georg Thieme Verlag, Stuttgart, 1994; T. W. Greene, P. G. M. Wuts, Protective Groups in Organic Synthesis, John Wiley & Sons, New York, 1999). Examples are silyl groups such as TBDMS, Acyl groups such as Acetyl or p-Methoxybenzyl groups.

In the following the invention is described in more detail with reference to examples. These examples are intended for illustration only and are not to be construed as any limitation.

EXAMPLES

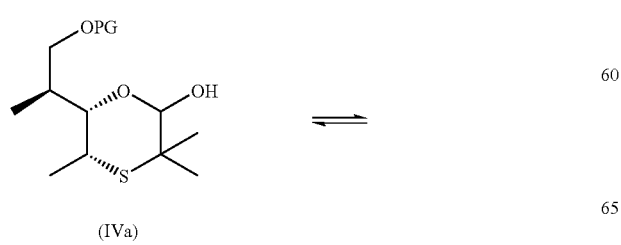

(IVa)

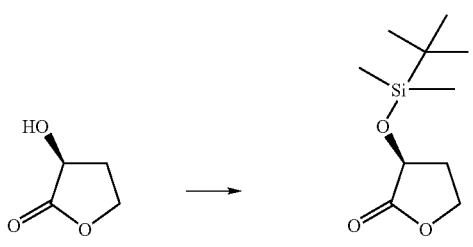

7

(3S)-3-(tert-Butyl-dimethyl-silanyloxy)-tetrahydro-furanone reproduced from *Chem. Eur. J.* 1999, 5, 2492, starting from commercially available (3S)-3-Hydroxytetrahydrofuran-2-one.

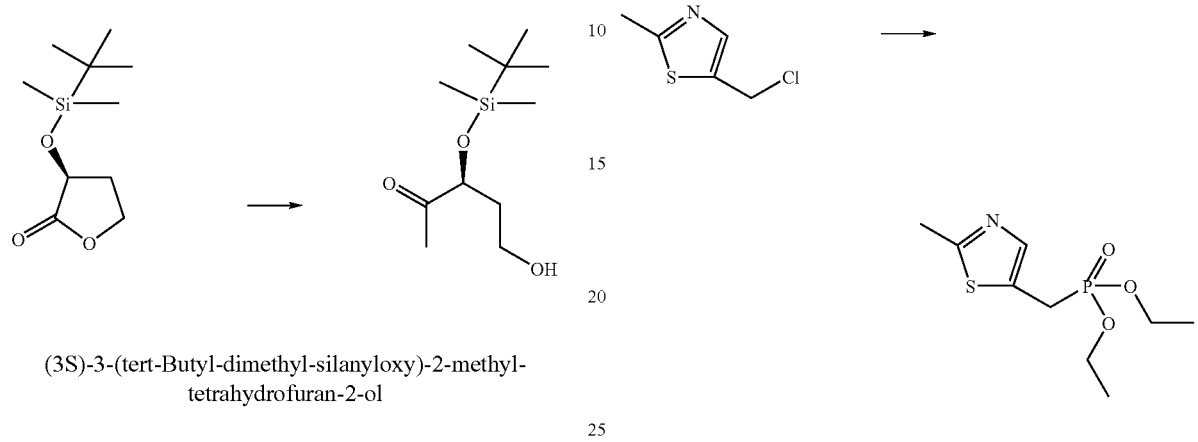

(3S)-3-(tert-Butyl-dimethyl-silanyloxy)-2-methyl-tetrahydrofuran-2-ol reproduced from *Chem. Eur. J.* 1999, 5, 2492

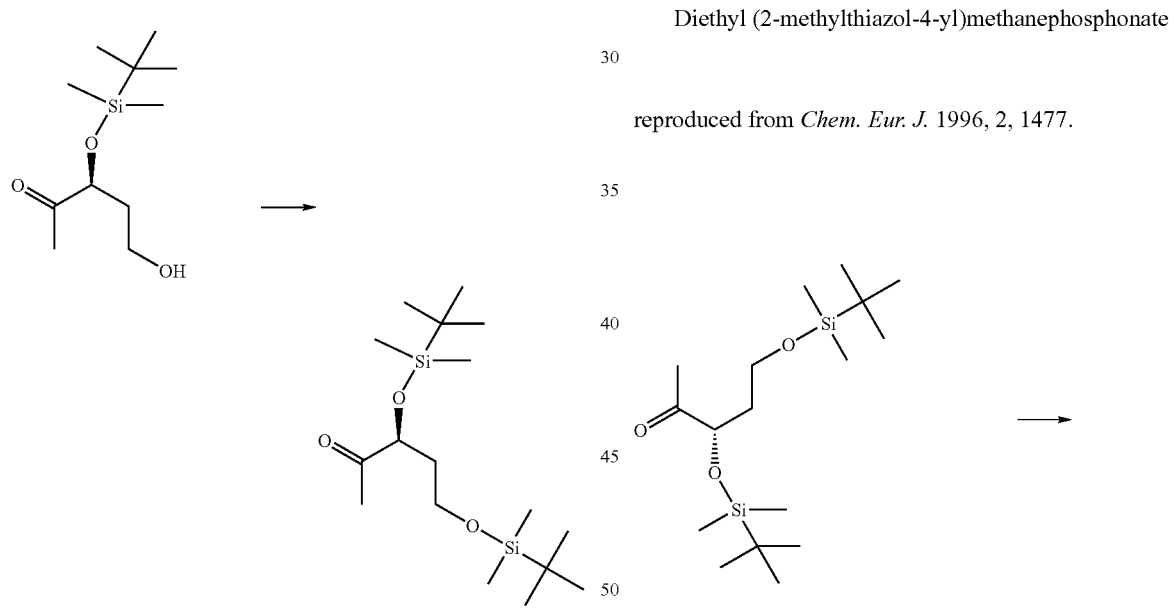

(3S)-3,5-Di-(tert-butyl-dimethyl-silanyloxy)-pentan-2-one reproduced from *Chem. Eur. J.* 1999, 5, 2492

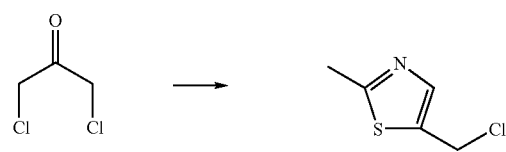

8

4-(Chloromethyl)-2-methyl-1,3-thiazole reproduced from *J. Org. Chem.* 2000, 65, 7456.

Diethyl (2-methylthiazol-4-yl)methanephosphonate reproduced from *Chem. Eur. J.* 1996, 2, 1477.

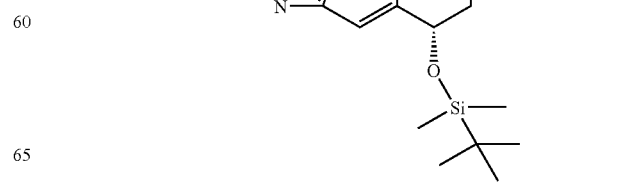

9

(3S,4E)-1,3-Di-(tert-butyl-dimethyl-silanyloxy)-4-methyl-5-(2-methyl-1,3-thiazol-4-yl)-4-pentene reproduced from *Chem. Eur. J.* 1996, 2, 1477.

10

(3S,4E)-3-(tert-Butyl-dimethyl-silanyloxy)-4-methyl-5-(2-methyl-1,3-thiazol-4-yl)-4-pentenal reproduced from *J. Org. Chem.* 2000, 65, 7456.

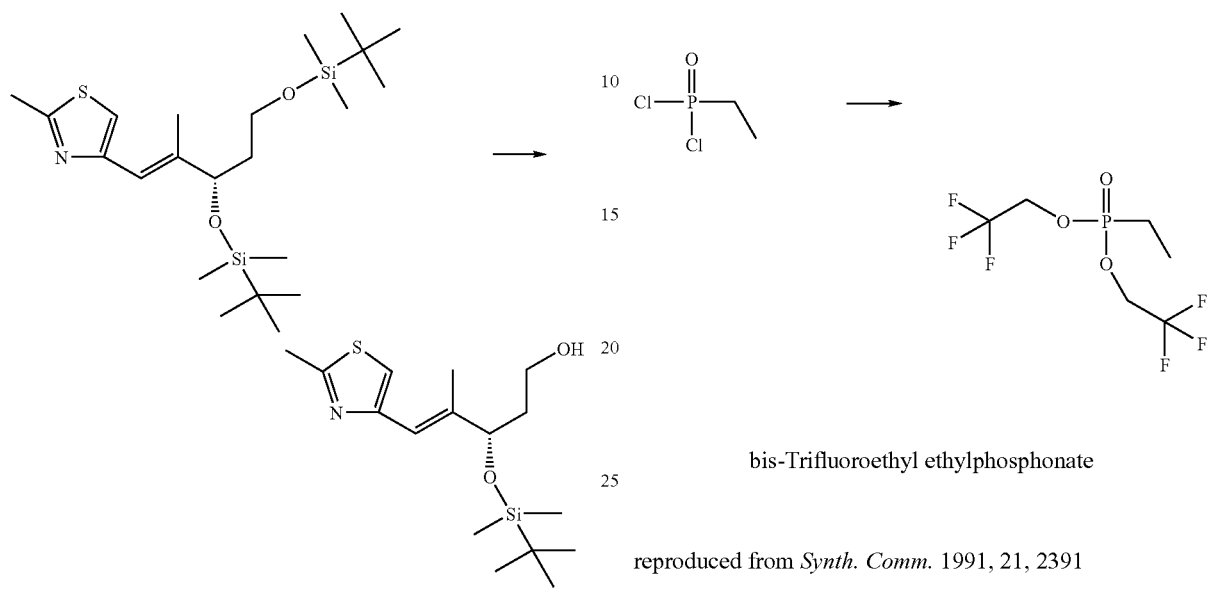

bis-Trifluoroethyl ethylphosphonate reproduced from *Synth. Comm.* 1991, 21, 2391

(3S,4E)-3-(tert-Butyl-dimethyl-silanyloxy)-4-methyl-5-(2-methyl-1,3-thiazol-4-yl)-4-penten-1-ol reproduced from *Chem. Eur. J.* 1996, 2, 1477.

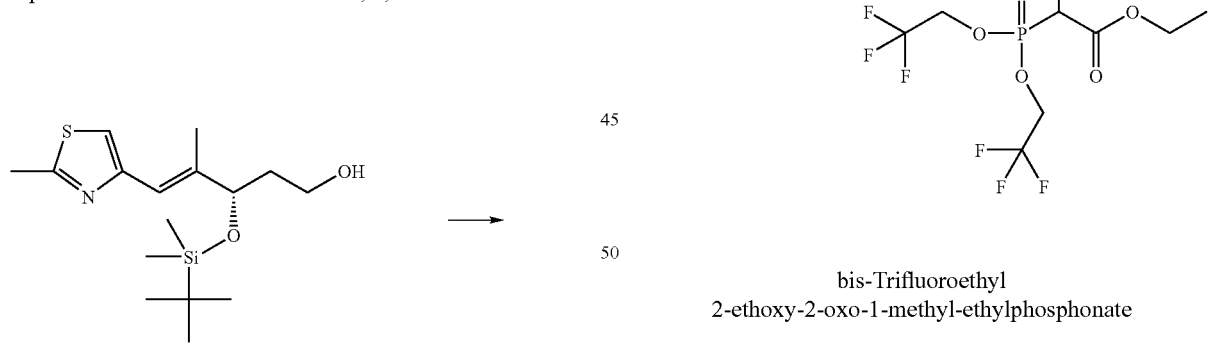

bis-Trifluoroethyl 2-ethoxy-2-oxo-1-methyl-ethylphosphonate reproduced from *Synth. Comm.* 1991, 21, 2391

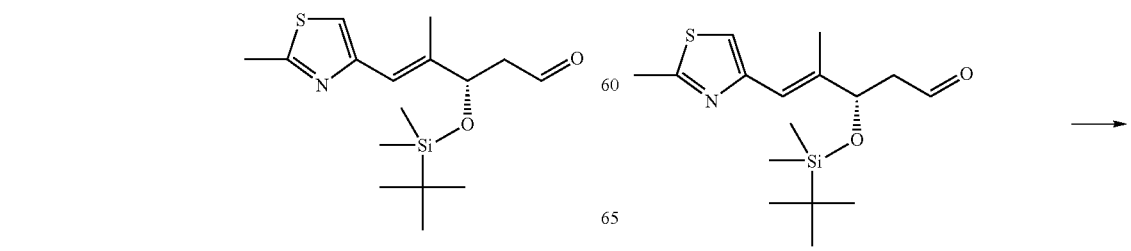

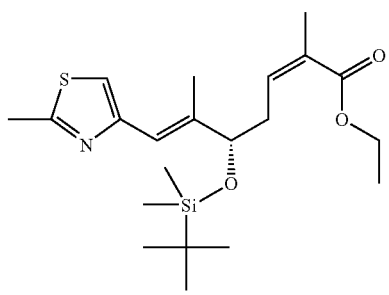

Ethyl (2Z,5S,6E)-5-(tert-Butyl-dimethyl-silanyloxy)-2,6-dimethyl-7-(2-methyl-1,3-thiazol-4-yl)-hepta-2,6-dienoate To a cooled solution of phosphonoacetate (5.12 g, 14.8 mmol) and 18-crown-6 (9.05 g) in tetrahydrofuran (142 mL) was added a solution of potassium bis(trimethylsilyl)amide (26.6 mL, 0.5M in toluene, 13.3 mmol) at −78° C. The cooling bath was removed and the reaction was stirred 15 minutes.

After cooling again to −78C, a solution of aldehyde (3.79 g crude, 11.7 mmol) in tetrahydrofuran (57 mL) was added drop wise over 60 minutes. The mixture was stirred one hour at this temperature. After warming, 10% NaHSO4 (100 mL) was added. The two phases were separated and the aqueous layer was extracted with ethyl acetate (3×100 mL). The combined organic layers were washed with brine and concentrated in vacuo. The residue was chromatographed (ethyl acetate-hexane 1:19) to afford the title ester (3.65 g, 8.9 mmol).

$^1$H NMR (CDCl3, 300 MHz): 6.93 (s, 1H); 6.52 (s, 1H); 5.98 (td, J=1.5, 7.3 Hz, 1H); 4.21 (t, J=5.5 Hz, 1H); 2.75 (m, 2H); 2.73 (s, 3H); 2.0 (s, 3H); 1.88 (s, 3H); 0.9 (s, 9H); 0.06 (s, 3H); 0.02 (s, 3H).

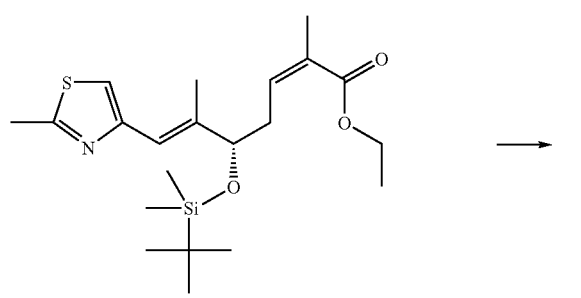

(2Z,5S,6E)-5-(tert-Butyl-dimethyl-silanyloxy)-2,6-dimethyl-7-(2-methyl-1,3-thiazol-4-yl)-hepta-2,6-dien-1-ol To a solution of ester (3.65 g, 8.9 mmol) in tetrahydrofuran (168 mL) was added dropwise diisobutyl aluminium hydride (27 mL; 1M in THF) at 0° C. The reaction mixture was then stirred at the same temperature for 90 minutes. The reaction was quenched by adding methanol (2 mL), diluted with ether (135 mL) and saturated K—Na tartrate (135 mL). The mixture was stirred at room temperature for 45 minutes. The two phases were separated and the aqueous layer was extracted with ether (3×150 mL). The combined ethereal layers were washed with brine and dried over sodium sulfate. The organic phase was filtered over a small pad of silica gel. The filtrate was concentrated in vacuo to afford the title alcohol (2.99 g, 8.1 mmol) as an oil.

$^1$H NMR (CDCl3, 300 MHz): 6.94 (s, 1H); 6.46 (s, 1H); 5.32 (td, J=2.5, 8.0 Hz, 1H); 4.13 (d, J=12 Hz, 1H); 4.11 (m, 1H); 4.01 (d, J=12 Hz, 1H); 2.72 (s, 3H); 2.46 (td, J=8.0, 14.1 Hz), 2.22 (m, 1H); 2.03 (d, J=1 Hz, 3H); 1.81 (s, 3H); 0.90 (s, 9H); 0.07 (s, 3H); 0.05 (s, 3H).

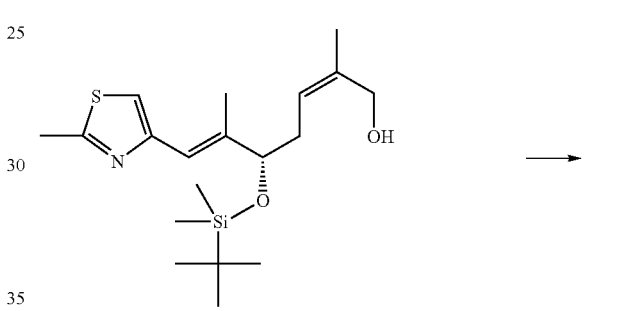

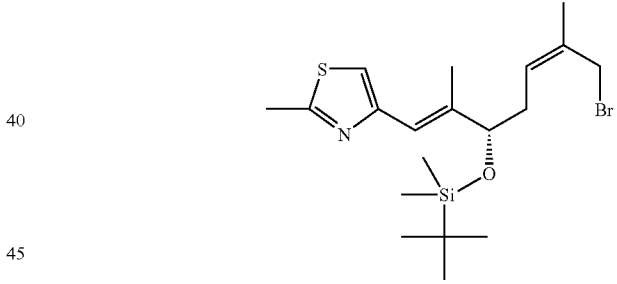

(3S)-4-[7-Bromo-3-(tert-butyl-dimethyl-silanyloxy)-2,6-dimethyl-hepta-1,5-dienyl]-2-methyl-thiazole reproduced from *J. Am. Chem. Soc.* 2001, 123, 5407.

To a solution of alcohol (1 g, 2.72 mmol) in dichloromethane (9 mL) were added at 0° C., triethylamine (0.581 mL, 4.16 mmol) and methanesulfonic anhydride (0.629 g, 3.6 mmol). After 10 minutes, acetone (9 mL) was added followed by lithium bromide (1.44 g, 16.73 mmol). The mixture was then stirred at room temperature for 40 minutes. The reaction mixture was diluted with dichloromethane and was filtered through hydromatrix (10% NaHSO4) and eluted with dichloromethane. The filtrate was concentrated in vacuo and the residue was columned (ethyl acetate-hexane 1:9) to afford the title bromide (0.868 g, 2 mmol).

$^1$H NMR (CDCl3, 300 MHz): 6.95 (s, 1H); 6.50 (s, 1H); 5.43 (td, J=1.6, 7.3 Hz, 1H); 4.16 (dd, J=5.4, 7.6 Hz, 1H); 4.06 (d, J=9.6 Hz, 1H); 3.90 (d, J=9.6 Hz, 1H); 2.73 (s, 3H);

2.39-2.33 (m, 2H); 2.03 (d, J=1 Hz, 3H); 1.84 (s, 3H); 0.9 (s, 9H); 0.06 (s, 3H); 0.02 (s, 3H).

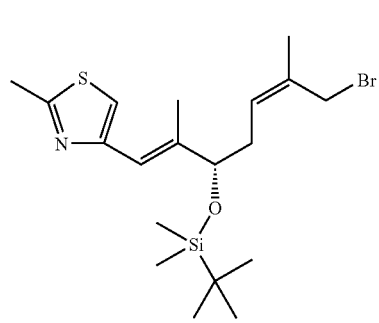

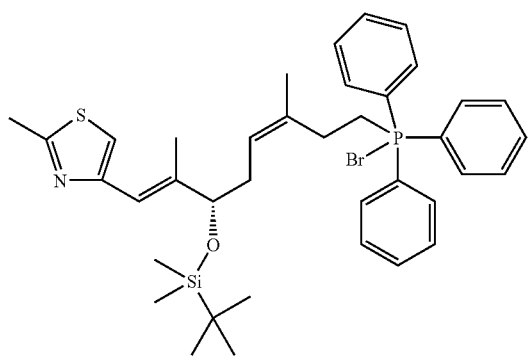

[(6S)-6-(tert-Butyl-dimethyl-silanyloxy)-3,7-dimethyl-8-(2-methyl1,3-thiazol-4-yl)-octa-3,7-dienyl]-triphenyl-phosphonium bromide reproduced from *J. Am. Chem. Soc.* 2001, 123, 5407.

To a solution of methyltriphenylphosphonium (3.16 g, 8.84 mmol) in tetrahydrofuran (30 mL) cooled to −78° C., was added n-butyllithium (3.8 mL, 2.3N in hexanes, 8.74 mmol). The reaction mixture was stirred for one hour at the same temperature and a pre-cooled (−78° C.) solution of bromide (0.868 g, 2 mmol) in tetrahydrofuran (13 mL+6 mL rinse) was introduced dropwise via a canula in the mixture. The reaction was then stirred one hour at this temperature and methanol (7 mL) was added. After evaporation to dryness, the residue was chromatographed (dichloromethane-methanol 19:1). The fractions containing the desired product were pooled and washed twice with water (2×150 mL). The organic layer was then dried over sodium sulfate and dried under reduced pressure to afford the title phosphonium (1.037 g, 1.47 mmol) as a foam.

¹H NMR (CDCl3, 300 MHz): 7.9-7.6 (m, 15H); 6.89 (s, 1H), 6.37 (s, 1H); 5.22 (m, 1H); 3.98 (m, 1H); 3.8-3.6 (m, 2H); 2.72 (s, 3H); 2.4-2.2 (m, 2H); 1.92 (s, 3H); 1.87 (s, 3H); 9.82 (s, 9H); −0.07 (s, 3H); −0.09 (s, 3H).

For the synthesis of the epoxides of the thioepothilone derivatives of the present invention, the epoxide of the above product can be synthesized according to standard procedures and then be used for the further synthesis.

2,2,2-Trichloro-acetimidic acid 4-methoxy-benzyl ester adapted from *Tetrahedron Letters*, 1996, 37, 1461

To a solution of 4-methoxy benzyl alcohol (17 g, 123 mmol) in dichloromethane (170 mL) was added 50% aqueous potassium hydroxyde solution (170 mL) and tetrabutylammonium hydrogen-sulfate (NBu4HSO4) (0.257 g). After cooling to −10C, tri-chloroacetonitrile (14.9 mL, 148 mmol) was added dropwise. The mixture was then stirred 30 minutes at the same temperature and then 30 minutes at room temperature. The two phases were separated and the aqueous layer was extracted twice with dichloromethane (2×170 mL). The combined organic layers were washed with brine and dried over sodium sulfate. The solvent was then removed under reduced pressure. The resulting oil was used in the next step without further purification.

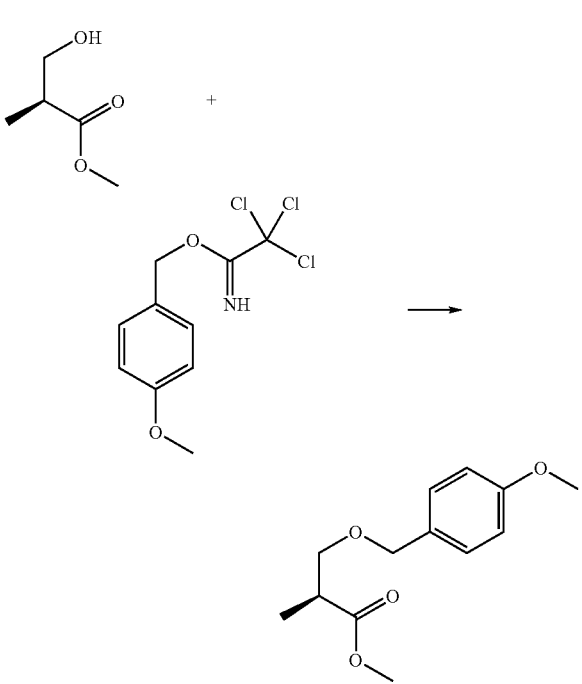

(2S)-3-(4-Methoxy-benzyloxy)-2-methyl-propionic acid methyl ester reproduced from *J. Am. Chem. Soc,* 2000, 122, 8654

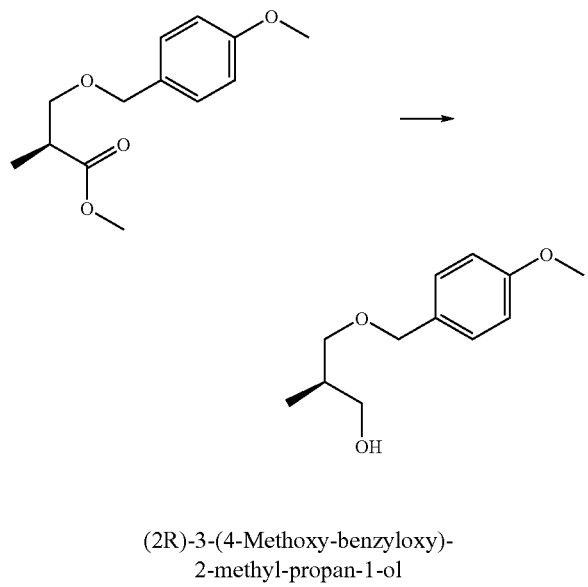

(2R)-3-(4-Methoxy-benzyloxy)-2-methyl-propan-1-ol reproduced from *J. Am. Chem. Soc,* 2000, 122, 8654

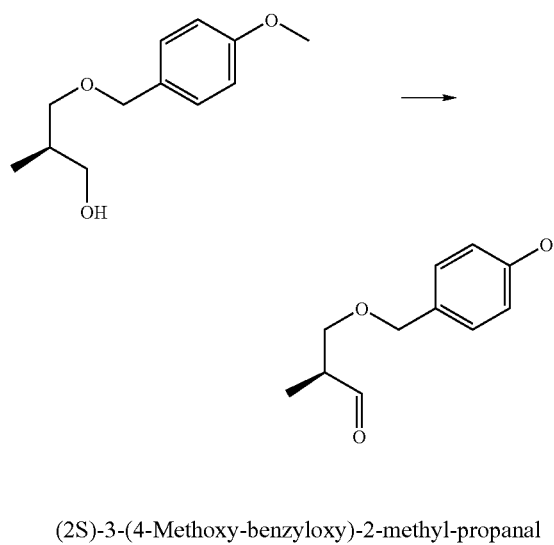

(2S)-3-(4-Methoxy-benzyloxy)-2-methyl-propanal reproduced from *J. Am. Chem. Soc,* 2000, 122, 8654

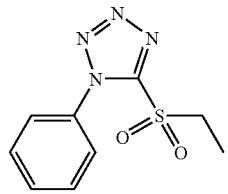

5-Ethylsulfonyl-1-phenyl-1H-tetrazole modified procedure taken from *J. Chem. Soc, Perkin Trans* 1, 1999, 955-968

To a solution of 1-Phenyl-5-mercaptotetrazole (25 g, 140 mmol) in ethanol (250 mL) was added powdered potassium hydroxide (9.5 g). The resulting mixture was refluxed for 1 h, and ethyl iodide (12 mL, 150 mmol) was added drop wise. The reaction proceeded under reflux for 18 h. After cooling, the volatiles were removed under reduced pressure and the residue was partitioned between water (300 mL) and ether (300 mL). The organic layer was washed with sat. NaHCO3 (2×120 mL) and brine (100 mL). After concentration in vacuo, the residue (28.71 g) was taken up in methanol (250 mL) and water (250 mL). After cooling to 0C, Oxone (400 g) was added portion wise. The mixture was then stirred for 1 h at room temperature before refluxing for 18 h. After cooling, ether (300 mL) was added and the solids were removed by filtration. The filtrate was then concentrated in vacuo, and the white solid was filtered. The latter was thoroughly washed with water and dried under reduced pressure over night to yield 5-Ethylsulfonyl-1-phenyl-1H-tetrazole (27.7 g, 116 mmol) as a white solid.

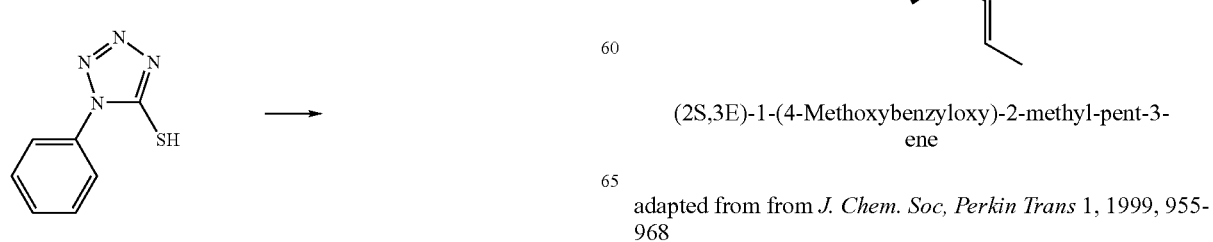

(2S,3E)-1-(4-Methoxybenzyloxy)-2-methyl-pent-3-ene adapted from from *J. Chem. Soc, Perkin Trans* 1, 1999, 955-968

To a stirred solution of the aldehyde (47.55 mmol) and 5-Ethylsulfonyl-1-phenyl-1H-tetrazole (13.61 g, 57.12 mmol) in 1,2-dimethoxyethane (305 mL), cooled to −60C, was added drop wise a solution of potassium bis(trimethylsilyl)amide (145 mL, 0.5M in toluene, 72.5 mmol) over 1 h (keeping the internal temperature between −60 and −70C). The reaction was then stirred for further 30 minutes. Water (36 mL) was then added and the reaction was allowed to warm up. The two phases were separated and the aqueous layer was extracted with ethyl acetate (3×100 mL). The combined organic layers were washed with brine and dried over magnesium sulfate. After evaporation to dryness, the residue was then chromatographed (ethyl acetate-hexane 1-19) to afford the title alkene as a 93-7 mixture (9.71 g, 44 mmol) as an oil.

$^1$H NMR (300 MHz, CDCl3): 7.27 (m, 2H); 6.88 (m, 2H); 5.44 (m, 2H); 4.47 (s, 2H); 3.33 (dd, J=6.6, 9.3 Hz, 1H); 3.24 (dd, J=7.2, 9.3 Hz, 1H); 2.44 (app p, J=6.9 Hz, 1H); 1.67 (dd, J=1.2, 6.0 Hz, 3H); 1.01 (d, J=6.6 Hz, 3H): $^{13}$C NMR (75 MHz, CDCl3): 159, 133.9, 130.7, 129.1 (2C), 124.5, 113.6 (2C); 75.2, 72.6, 55.2, 36.8, 18.0, 17.3.

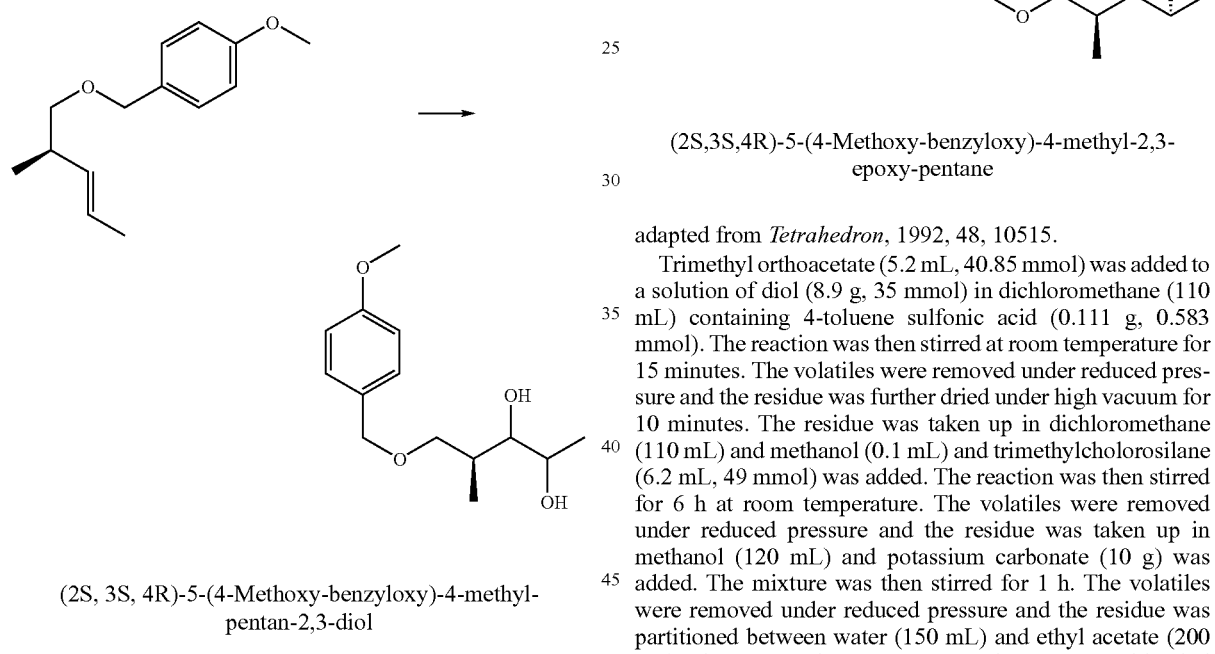

(2S, 3S, 4R)-5-(4-Methoxy-benzyloxy)-4-methyl-pentan-2,3-diol

To a vigorously stirred mixture of 2-methyl-2-propanol (140 mL) and water (165 mL) were added AD mix alpha or beta, respectively (58 g) and methanesulfonamide (4.17 g, 43.8 mmol). The resulting clear solution was then cooled down to 0° C., and a solution of alkene (9.67 g, 44 mmol) in 2-methyl-2-propanol (20 mL+7 mL rinse) was added. The mixture was further stirred at 0C for 18 h. Sodium pyrobisulfite (60 g) was added portion wise. The resulting clear phases were separated and the aqueous layer was extracted twice with ethyl acetate (2×200 mL). The combined organic layers were washed with brine, dried over sodium sulfate and then concentrated in vacuo. The residue was purified over silica gel (ethyl acetate-hexane 2-1) to afford the title diol (9.11 g, 35.5 mmol) as an oil.

MS (ESI, m/z):277.3 [M+Na]$^1$H NMR (300 MHz, CDCl3): 7.26 (m, 2H); 6.89 (m, 2H); 4.44 (dd, AB; J=11.9, 12.6 Hz, 2H); 3.81 (s, 3H); 3.79 (m overlapped, 1H); 3.55 (dd, J=3.9, 9.3 Hz, 1H); 3.42 (m, 2H); 2.50 (br s, 2H); 1.90 (m, 1H); 1.16 (d, J=6.4 Hz, 3H); 0.96 (d, J=7.14 Hz, 3H). $^{13}$C NMR (75 MHz, CDCl3): 159.2, 129.8, 129.2 (2C), 113.7 (2C), 79.4, 73.3, 72.9, 67.8, 55.2, 35.7, 19.0, 11.8.

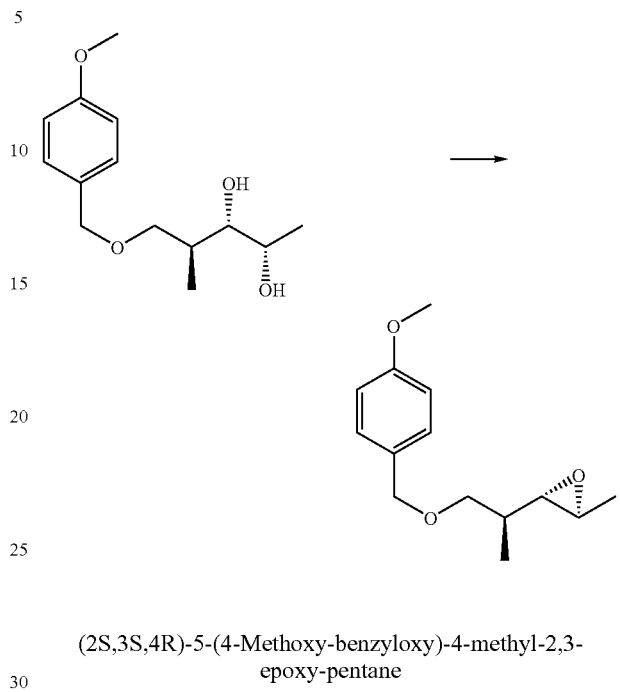

(2S,3S,4R)-5-(4-Methoxy-benzyloxy)-4-methyl-2,3-epoxy-pentane adapted from *Tetrahedron*, 1992, 48, 10515.

Trimethyl orthoacetate (5.2 mL, 40.85 mmol) was added to a solution of diol (8.9 g, 35 mmol) in dichloromethane (110 mL) containing 4-toluene sulfonic acid (0.111 g, 0.583 mmol). The reaction was then stirred at room temperature for 15 minutes. The volatiles were removed under reduced pressure and the residue was further dried under high vacuum for 10 minutes. The residue was taken up in dichloromethane (110 mL) and methanol (0.1 mL) and trimethylcholorosilane (6.2 mL, 49 mmol) was added. The reaction was then stirred for 6 h at room temperature. The volatiles were removed under reduced pressure and the residue was taken up in methanol (120 mL) and potassium carbonate (10 g) was added. The mixture was then stirred for 1 h. The volatiles were removed under reduced pressure and the residue was partitioned between water (150 mL) and ethyl acetate (200 mL). The aqueous layer was extracted once more with ethyl acetate (200 mL). The combined organic layers were washed with brine (50 mL), dried over sodium sulfate and evaporated to dryness. The residue was purified by chromatography (ethyl acetate-hexane 1-6) to afford the title epoxide (5.0 g, 21.15 mmol) as an oil.

$^1$H NMR (300 MHz, CDCl3): 7.27 (m, 2H); 6.89 (m, 2H); 4.44 (s, 2H); 3.81 (s, 3H); 3.40 (m, AB, 2H); 2.87 (dq, J=2.3, 5.2 Hz, 1H); 2.57 (dd, J=2.3, 6.81 Hz, 1H); 1.72 (app hept, J=6.8 Hz, 1H), 1.29 (d, J=5.2 Hz, 3H); 0.99 (d, J=6.8 Hz, 3H).

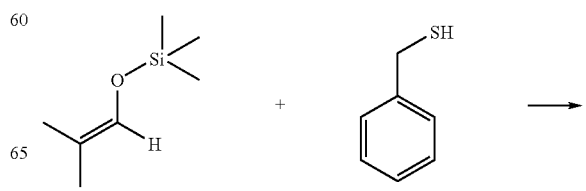

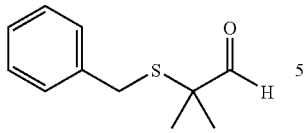

2-Benzylsulfanyl-2-methyl-propionaldehyde

Sulfuryl chloride (13.2 mL, 162 mmol) was added drop wise to a solution of benzyl mercaptan (19.2 mL, 162 mmol) and pyridine (13.2 mL, 164 mmol) in dichloromethane (810 mL) at −78° C. The reaction mixture was stirred for 15 minutes whereupon a precipitate formed. The reaction mixture was warmed to 0° C. for 30 min. and a clear solution evolved. After cooling −78° C., a solution of 2-methyl-trimethylsilyloxypropene (30 mL, 163.2 mmol) in tetrahydrofuran (810 mL) was added slowly over 1 h. The reaction mixture was further stirred at −78° C. for 1 h, then warmed to 0° C., and stirred for 30 minutes. The solvent was removed under reduced pressure. The residue was taken up in ether (200 mL) and the resulting solution was filtered over a small pad of silica gel. The solvent was then removed to afford crude aldehyde (31.2 g) as an oil. The title aldehyde was then carried on without further purification.

$^1$H NMR (300 MHz, CDCl3): 9.13 (s, 1H); 7,26 (m, 5H); 3.51 (s, 2H); 1.39 (s, 6H).

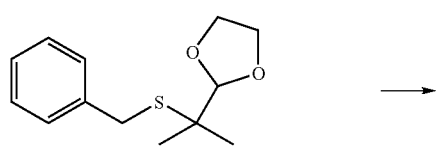

2-(1-Benzylsulfanyl-1-methyl-ethyl)-[1,3]dioxolane

A solution of crude aldehyde (31.2 g, 160.6 mmol) and ethylene glycol (20 g, 322 mmol) in toluene (300 mL) containing p-TsOH (1.5 g, 7.8 mmol) was refluxed for 4 h using a Dean-Stark trap to remove the water formed. After cooling, triethylamine (3 mL, 21 mmol) was added. The volatiles were removed under reduced pressure and the residue was chromatographed (hexane-ethyl acetate 49-1 then 9-1) to afford the title ketal (32.4 g, 136 mmol) as an oil.

$^1$H NMR (300 MHz, CDCl3): 7.29 (m, 5H); 4.86 (s, 1H); 3.96 (m, 4H); 3.94 (s, 2H); 1.31 (s, 6H).

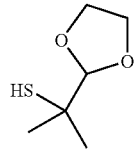

2-[1,3]Dioxolan-2-yl-propane-2-thiol

Finely divided sodium metal (8.08 g, 351 mmol) was added portion wise to condensed ammonia (800 mL) whereupon a intense blue color appeared. A solution of ketal (32.4 g, 136 mmol) in tetrahydrofuran (212 mL) was added drop wise. After 20 minutes, the reaction mixture was quenched with ethanol (70 mL) until the blue color disappeared. Ether (300 mL) was added to the mixture which was allowed to warm up at room temperature. After NH3 was completely evaporated, the reaction mixture was washed with sat NH4Cl (100 mL) and brine (100 mL). The organic phase was dried over magnesium sulfate and then filtered over a pad of silica gel. The filtrate was concentrated to dryness to afford the title compound contaminated with dihydrostilbene. The material was further dried for 10 minutes under high vacuum to afford the title thiol (18.36 g)

$^1$H NMR (300 MHz, CDCl3): 4.85 (s, 1H); 4.00 (s, 1H); 3.94 (m, 4H); 1.30 (s, 6H).

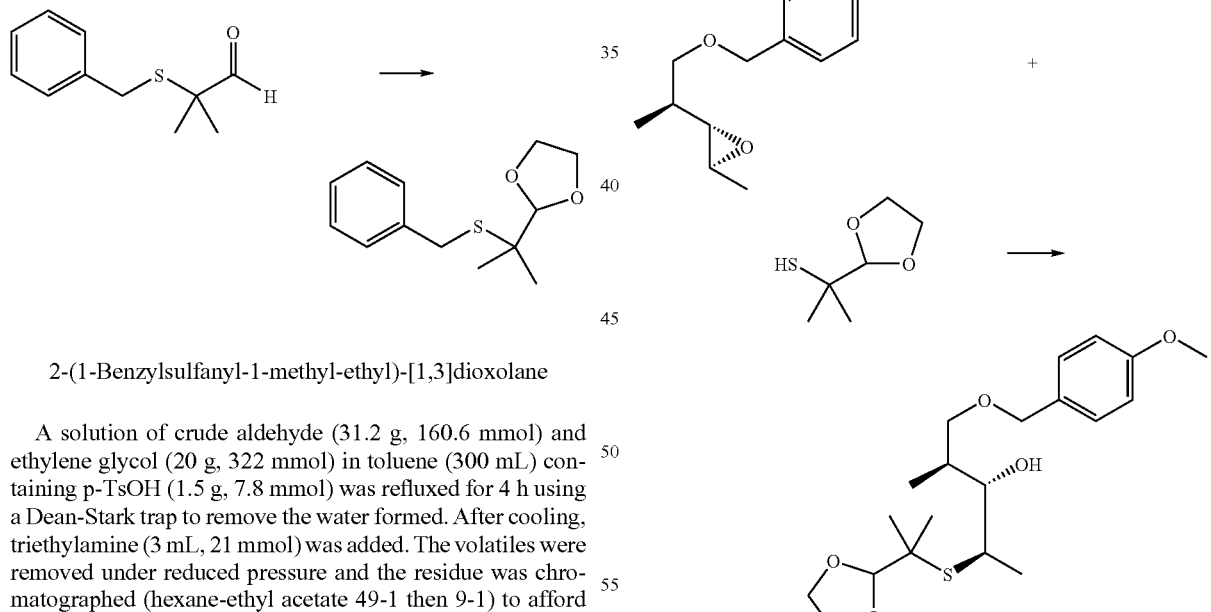

(2R,3S,4R)-4-(1-[1,3]Dioxolan-2-yl-1-methyl-ethyl-sulfanyl)-1-(4-methoxy-benzyloxy)-2-methyl-pentan-3-ol To a suspension of sodium hydride (3 eq., 60% in dispersion, unwashed) in N,N-dimethylformamide (4 mL/mmol) was added crude thiol (3 eq.) at 0° C. The mixture was stirred at room temperature for 30 minutes, and a solution of the epoxide (1 eq.) in N,N-dimethylformamide was then added. The reaction mixture was heated at 80° C. (temperature in the flask 1) for at least 17 h. Water (95 mL) was added and the mixture was concentrated to dryness under high vacuum. The residue was partitioned between water (200 mL) and ethyl acetate (200 mL). The aqueous layer was extracted three times with ethyl acetate (3×200 mL). The combined organic extracts were washed with brine and dried over magnesium sulfate. After concentration in vacuo, the residue was chromatographed (ethyl acetate-hexane 1:3) to afford the title alcohol as an oil.

$^1$H NMR (300 MHz, CDCl3): 7.27 (m, 2H); 6.89 (m, 2H); 4.79 (s, 1H); 4.44 (s, 2H); 3.91 (m, 4H); 3.81 (s, 3H); 3.68 (t, J=5.4 Hz, 1H); 3.44 (m, 2H); 3.32 (m, 1H); 2.07 (m, 1H); 1.59 (br s, 1H); 1.33 (d, J=11.4 Hz, 3H); 1.31 (s, 3H), 1.29 (s, 3H), 1.03 (d, J=6.9 Hz, 3H).

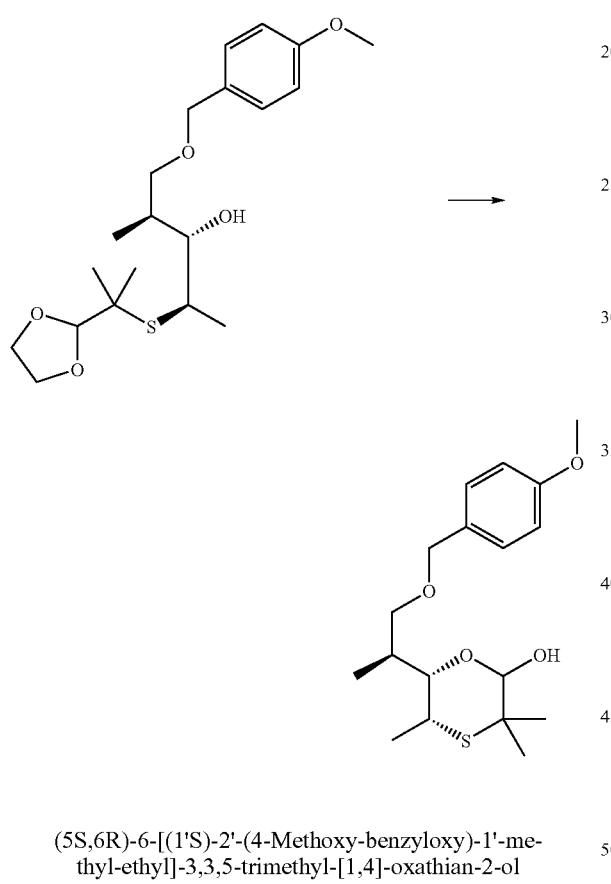

(5S,6R)-6-[(1'S)-2'-(4-Methoxy-benzyloxy)-1'-methyl-ethyl]-3,3,5-trimethyl-[1,4]-oxathian-2-ol To a solution of ketal (1.15 g, 3 mmol) in tetrahydrofuran (12 mL) was added 2M H2SO4 (2.8 mL). The reaction mixture was heated at 60C for 3 h. The reaction mixture was cooled down. Water (10 mL) and ether (30 mL) were added. The aqueous layer was discarded and the organic layer was washed with water until pH=7 was reached. The organic layer was then filtered through hydromatrix (Sat NaHCO3, water) and the filtrate was concentrated in vacuo. The residue was then chromatographed (hexane-ethyl acetate 4-1 then 2-1) to afford the hemiacetal (0.970 g, 2.84 mmol) as an oil.

$^1$H NMR (300 MHz, CDCl3) main epimer: 7.23 (m, 2H); 6.87 (m, 2H); 4.75 (d, J=5.4 Hz, 1H); 4.40 (dd, AB, J=11.7, 15.3 Hz, 2H); 3.85 (dd, J=2.4, 9.6 Hz, 1H); 3.80 (s, 3H); 3.30 (app qd, J=5.1, 9.6 Hz, 2H); 2.69 (d, J=5.7 Hz, 1H); 2.65 (qd, J=2.4, 7.2 Hz, 1H); 1.89 (m, 1H); 1.48 (s, 3H); 1.44 (d, J=7.2 Hz, 3H); 1.16 (s, 3H); 1.1 (d, J=6.6 Hz, 3H).

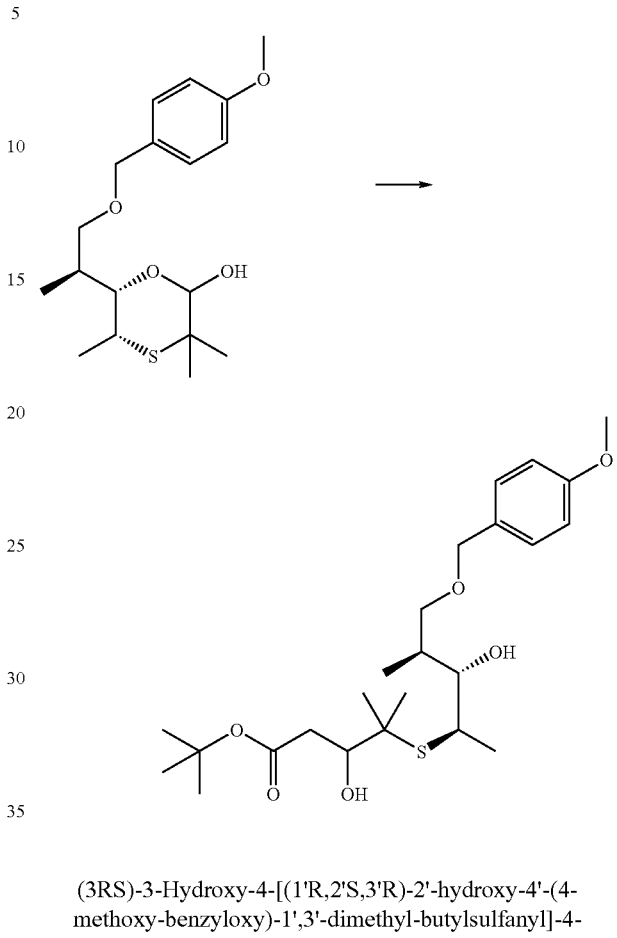

(3RS)-3-Hydroxy-4-[(1'R,2'S,3'R)-2'-hydroxy-4'-(4-methoxy-benzyloxy)-1',3'-dimethyl-butylsulfanyl]-4-methyl-pentanoic acid tert-butyl ester To a solution of diisopropylamine (5.1 mL, 36.4 mmol) in tetrahydrofuran (90 mL) was added at −78C, n-BuLi (14 mL, 2.3N in hexane, 32.2 mmol). The solution was stirred 5 minutes at this temperature and then 10 minutes at 0C. After cooling to −78C, tert-butyl acetate (5.6 mL, 41.5 mmol) was added drop wise over 15 minutes. The resulting mixture was then stirred 1 h at the same temperature and a solution of lactol (1.5 g, 4.4 mmol) in tetrahydrofuran (3 mL+1 mL rinse) was added. The mixture was then stirred 15 minutes at −78C, and the reaction mixture was warmed to 0C. The reaction proceeded at this temperature for 2 h and then 1 h at room temperature. The reaction was quenched by adding water. The reaction mixture was extracted with ethyl acetate (2×100 mL). The combined organic layers were dried over sodium sulfate and concentrated in vacuo. The residue was chromatographed over silica gel (hexane-ethyl acetate 3-1) to afford the title ester (1.15 g, 2.51 mmol) as an oil.

MS (ESI, m/z): 457.9 [M+H$^+$]$^1$H NMR (300 MHz, CDCl3): 7.25 (m, 2H); 6.86 (m, 2H); 4.42 (br s, 2H); 3.91 (two dd, 1H); 3.81 (two s, 3H); 3.67 (m, 1H); 3.66 (m, 2H); 3.17 (m, 1H); 2.58 (td, 1H); 2.40 (m, 1H); 2.2 (br s, 20H); 2.06 (m, 1H); 1.46 (two s, 9H); 1.30-1.25 (m, 9H); 1.12 (m, 3H).

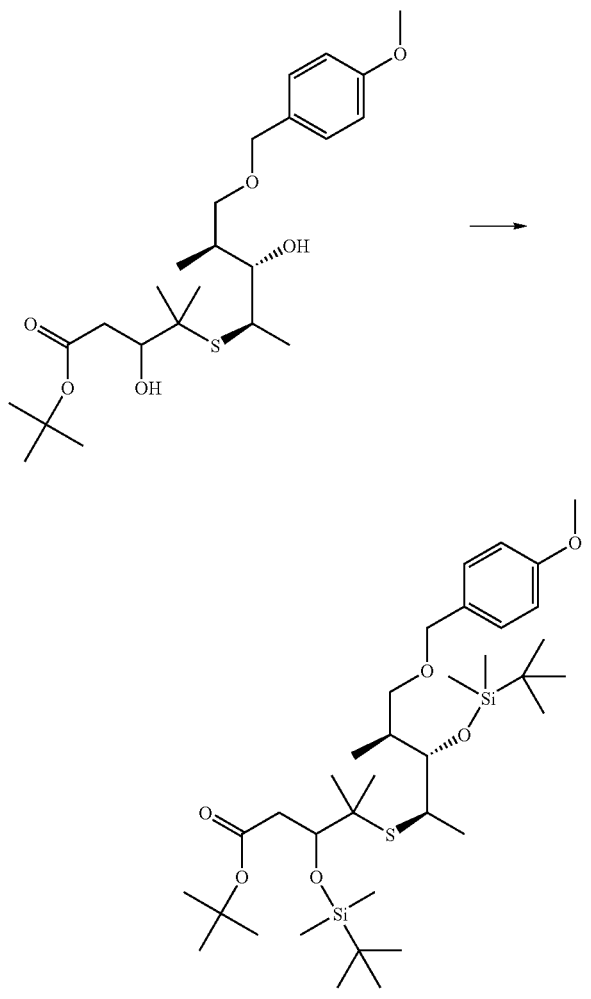
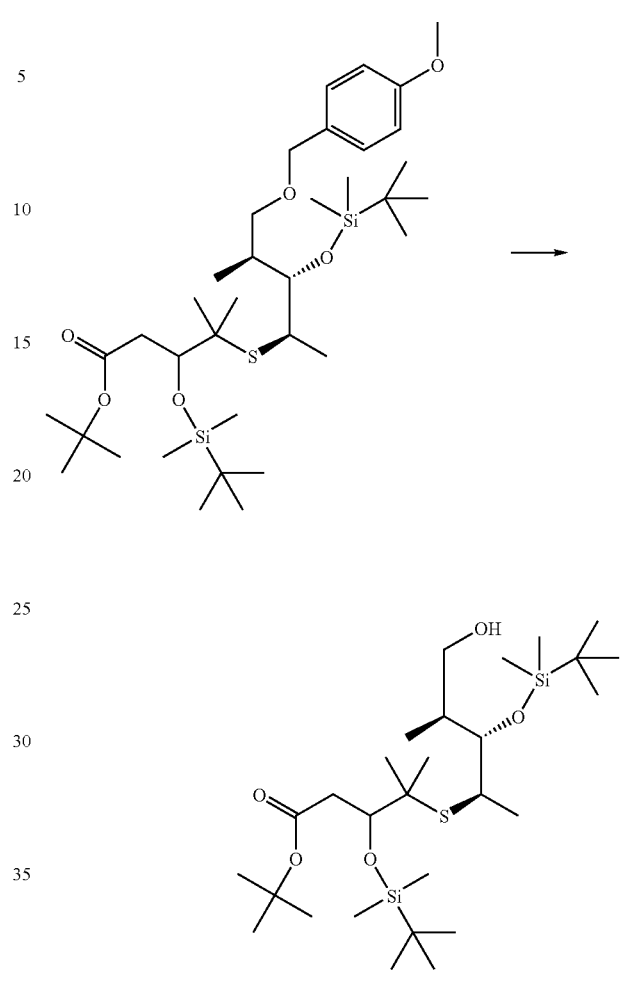

(3RS)-3-(tert-Butyl-dimethyl-silanyloxy)-4-[(1'R, 2'S,3'S)-2'-(tert-butyl-dimethyl-silanyloxy)-4'-(4-methoxy-benzyloxy)-1',3'-dimethyl-butylsulfanyl]-4-methyl-pentanoic acid tert-butyl ester To a solution of diol (1.15 g, 2.51 mmol) in dichloromethane (18 mL), cooled to −78C, were added 2,6-lutidine (2 mL 2.88 mL, 24.76 mmol) and tert-Butyldimethylsilyl trifluoromethane-sulfonate (3.45 mL, 15 mmol). The reaction mixture was then stirred 15 minutes at this temperature and then warmed up to 0C. The reaction proceeded for 1 h, and was diluted with diethyl ether (150 mL) and saturated CuSO4 (30 mL). The organic layer was then further washed with saturated CuSO4 (5×30 mL), water (30 mL) and brine (30 mL). After drying over sodium sulfate and evaporation to dryness, the title crude compound was recovered as a yellowish oil around (2.2 g). This material was carried on without further purification.

$^1$H NMR (300 MHz, CDCl3): 7.26 (m, 2H); 6.89 (m, 2H); 4.42 (br, s, 2H); 4.19 (m, 0.6H); 4.12 (m, 0.4H); 3.80 (s and overlapped m, 3.6H); 3.74 (m, 0.4H); 3.44-3.2 (m, 4H); 2.36-2.25 (m, 1H); 2.13 (m, 1H); 1.44 (two s, 3H); 1.24 (m, 6H); 0.98-0.86 (m, 30H); 0.28-0.02 (m, 12H).

(3RS)-3-(tert-Butyl-dimethyl-silanyloxy)-4-[(1'R, 2'S,3'S)-2'-(tert-butyl-dimethyl-silanyloxy)-4'-hydroxy-11,3'-dimethyl-butylsulfanyl]-4-methyl-pentanoic acid tert-butyl ester To a solution of ester (2.2 g, crude, 2.51 mmol) in dichloromethane (17 mL) and water (1 mL) was added 2,3-dichloro-5,6-dicyano-p-benzoquinone (DDQ) (0.72 g, 3.17 mmol). The reaction was stirred at room temperature for 30 minutes and diethyl ether (250 mL) and saturated NaHCO3 (50 mL) were added. The organic layer was further washed with saturated NaHCO3 until clear aqueous layer was obtained. The organic layer was washed with brine and dried over sodium sulfate. After evaporation to dryness, the residue was chromatographed (hexane-ethyl acetate 9-1) to afford the title alcohol (1.4 g, 2.47 mmol) as an oil.

$^1$H NMR (300 MHz, CDCl3): 4.18 (dd, J=2.7, 6.6 Hz, 0.5H); 4.13 (td, J=3.3, 6.9 Hz, 0.5H); 3.86 (m, 1H); 3.55 (m, 2H); 3.25 (ddd, J=2.4, 17.4, 34.5 Hz, 0.5H), 3.21 (dd, J=2.4, 17.1 Hz, 0.5H), 3.06 (m, 1H); 2.29 (m, 1H); 2.1 (m, 0.5H); 1.95 (m, 0.5H), 1.46 (s, 6H); 1.35-1.15 (m, 6H); 0.98-0.89 (m, 27H); 0.2-0.03 (m, 12H).

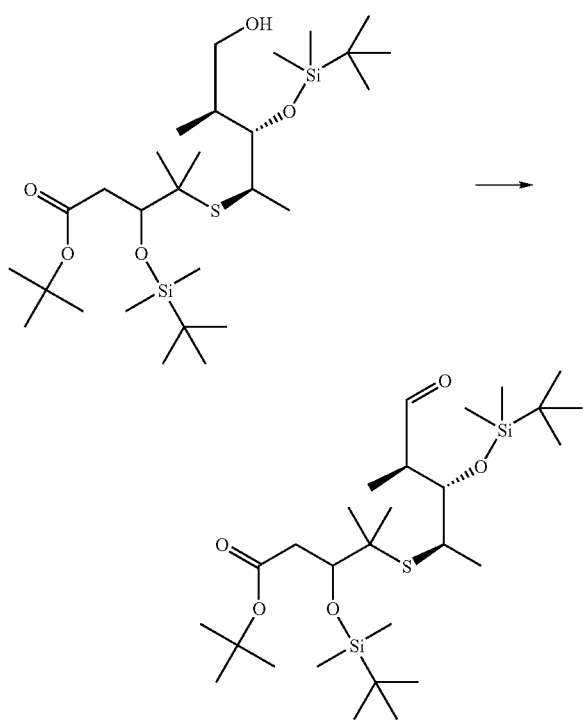

(3RS)-3-(tert-Butyl-dimethyl-silanyloxy)-4-[(1'R, 2'S,3'S)-2'-(tert-butyl-dimethyl-silanyloxy)-1,3-dimethyl-4-oxo-butylsulfanyl]-4-methyl-pentanoic acid tert-butyl ester To a solution of oxalyl chloride (0.59 mL, 7 mmol) in dichloromethane (6 mL) cooled to −78C, was added a solution of DMSO (0.6 mL, 8.4 mmol) in dichloromethane (6 mL). The reaction was stirred 15 minutes at room temperature and a solution of alcohol (1.4 g, 2.47 mmol) in dichloromethane (5 ml+2 mL rinse) was added. After stirring for one hour at the same temperature, a solution of diisopropylethylamine (3 mL, 17.52 mmol) in dichloromethane (3 mL) was added. The reaction was stirred for 20 minutes and then was warmed to 0° C. After stirring 30 minutes, TLC showed that the reaction was complete and the reaction mixture was filtered through hydromatrix and the filtrate was concentrated in vacuo. The residue was then chromatographed (hexane-ethyl acetate 9-1) to afford the title compound (1.22 g, 2.16 mmol) as an oil. The aldehyde was immediately used in the next step without characterization.

Completion of the Synthesis:

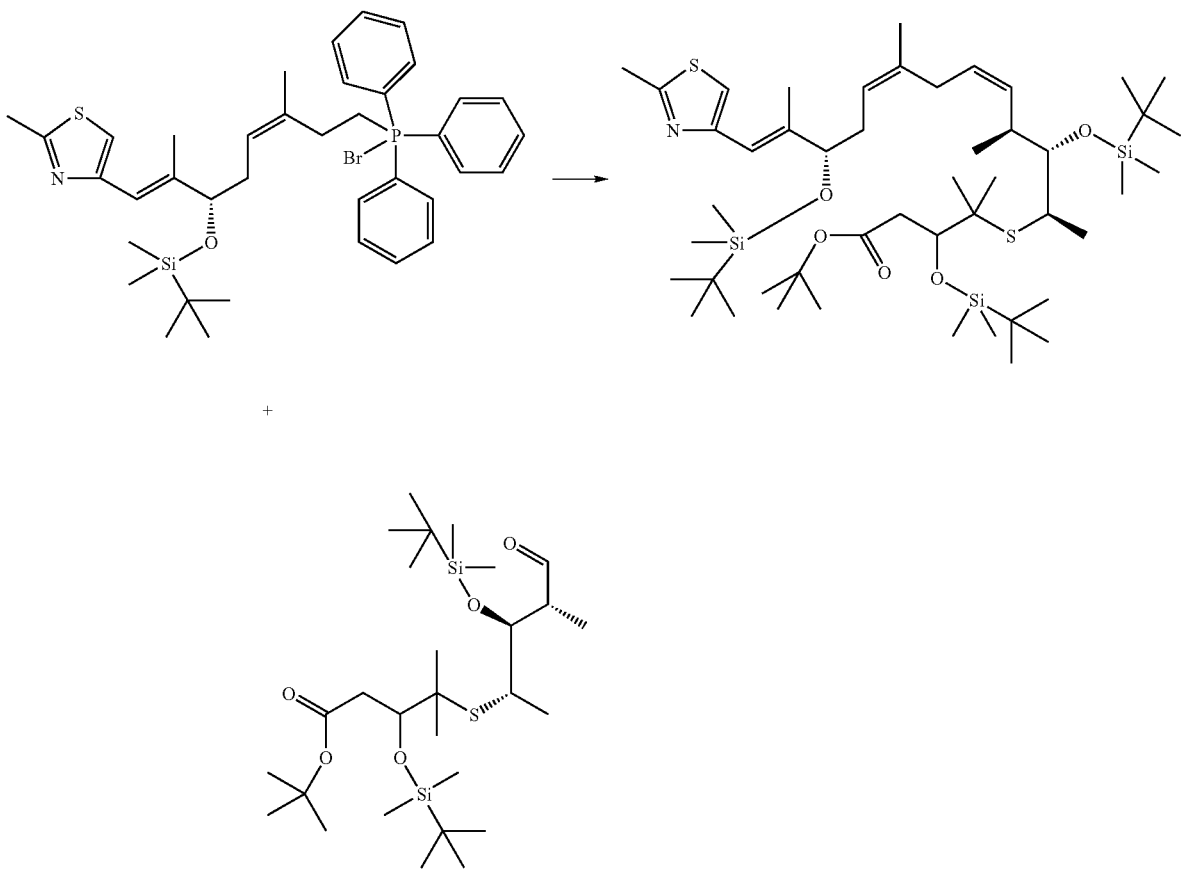

(3RS)-4-[(1'R,2'S,3'S,4'Z,7'Z,10'S,11'E)-2',10'-Bis-(tert-butyl-dimethyl-silanyloxy)-1',3',7',11'-tetramethyl-12'-(2-methyl-thiazol-4-yl)-dodeca-4',7',11'-trienylsulfanyl]-3-(tert-butyl-dimethyl-silanyloxy)-4-methyl-pentanoic acid tert-butyl ester To a solution of [(6S)-6-(tert-Butyl-dimethyl-silanyloxy)-3,7-dimethyl-8-(2-methyl1,3-thiazol-4-yl)-octa-3,7-dienyl]-triphenyl-phosphonium bromide (2.57 g, 3.64 mmol) in tetrahydrofuran (47 mL) cooled to −78C, was added a solution of lithium bis trimethylsilyl amide (3.5 mL, 1.06M in tetrahydrofuran, 3.71 mmol). The mixture was then stirred for 1 h at −78C. A solution of aldehyde (1.2 g, 2.13 mmol) in tetrahydrofuran (5 mL+3 mL rinse) was added dropwise to the mixture. The reaction was stirred for one hour at −78 C and warmed up to 0 C. The reaction mixture was then stirred for 1 h. No more evolution was stated by TLC. The reaction mixture was quenched by adding MeOH (5 mL). Sodium borohydride (0.4 g, 10.6 mmol) was added to reduce the remaining aldehyde, The mixture was stirred for 20 minutes. Water (40 mL) was then added and the two phases were diluted with ethyl acetate and separated. The aqueous layer was extracted with ethyl acetate (4×50 mL). The combined organic layers were washed with brine and dried over sodium sulfate. The filtrate was concentrated in vacuo and chromatographed (ethyl acetate-hexane 1:30) to afford the title compound (1.0 g, 1.1 mmol) as an oil.

$^1$H NMR (300 MHz, CDCl3): 6.92 (s, 1H); 6.48 (s, 1H); 5.53 (m, 0.5H); 5.31-5.14 (m, 2.5H); 4.11 (m, 2H); 3.58 (m, 1H); 3.21 (m, 1H); 3.01 (m, 1H); 2.83-2.78 (m, 2H); 2.72 (s, 3H); 2.70 (m, 0.5H); 2.34-2.12 (m, 3.5H); 2.00 (s, 3H); 1.67 (s, 3H); 1.46 (s, 4.5H); 1.44 (s, 4.5H); 1.43 (s, 1.5H); 1.33 (s, 1.5H); 1.18 (overlapped signals, 3H); 1.10 (s, 3H); 1.00 (d, J=7.0 Hz, 3H); 0.92 (s, 4.5H); 0.91 (s, 4.5H); 0.88 (s, 9H); 0.86 (s, 9H); 0.19 (s, 1.5H); 0.18 (s, 1.5H); 0.1-0.001 (several s, 15H).

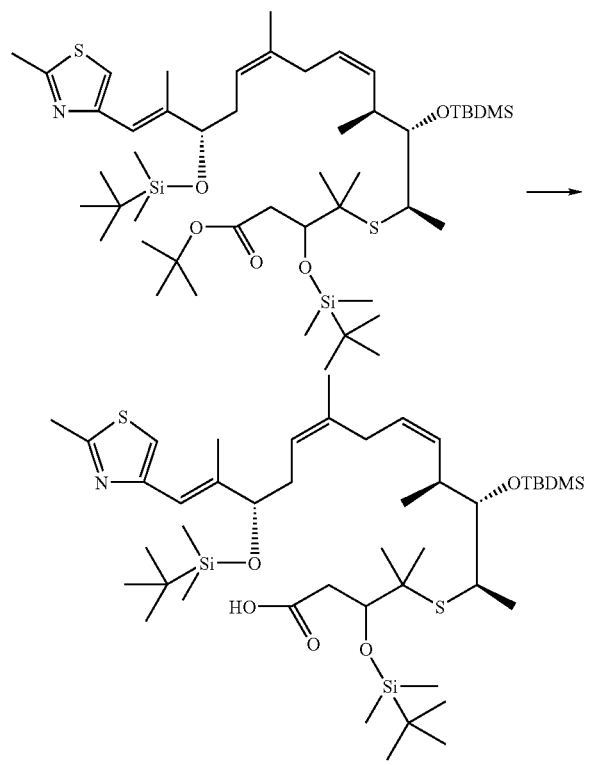

(3R)-4-[(1'R,2'S,3'S,4'Z,7'Z,10'S,11'R)-2',10'-Bis-(tert-butyl-dimethyl-silanyloxy)-1',3',7',11'-tetramethyl-12'-(2-methyl-thiazol-4-yl)-dodeca-4',7',11'-trienylBulfanyl]-3-(tert-butyl-dinethyl-silanyloxy)-4-methyl-pentanoic acid and (3S)-4-[(1'R,2'S,3'S,4'Z,7'Z,10'S,11'E)-2',10'-Bis-(tert-butyl-dimethyl-silanyloxy)-1',3',7',11'-tetramethyl-12'-(2-methyl-thiazol-4-yl)-dodeca-4',7',11'-trienylsulfanyl]-3-(tert-butyl-dimethyl-silanyloxy)-4-methyl-pentanoic acid To an ice-chilled solution of substrate (11.0 g, 1.1 mmol) in dichloromethane (78 mL) were added 2,6-lutidine (1.63 mL, 14.1 mmol) and then trimethylsilyl trifluoromethane-sulfonate (1.27 mL, 7 mmol). The reaction was stirred at the same temperature for 1 h. The reaction mixture was then warmed up to room temperature and further stirred for 3 h. The reaction mixture was then diluted with diethyl ether (300 mL). The organic layer was washed with a saturated solution of copper sulfate (5×80 mL), brine (80 mL) and dried over magnesium sulfate. The residue was chromatographed (hexane-ethyl acetate 9-1) to afford a first eluting isomer (0.400 g, 0.468 mmol) as an oil.

$^1$H NMR (300 MHz, CDCl3): 6.97 (s, 1H); 6.80 (s, 1H); 5.37-5.3 (m, 3H); 4.26 (dd, J=1.8, 7.8 Hz, 1H); 4.21 (dd, J=4.5, 9.0 Hz, 1H); 3.65 (d, J=9.3 Hz, 1H); 3.40 (dd, J=1.8, 16.0 Hz, 1H); 3.20 (app q, J=6.9 Hz, 1H); 3.11 (m, 1H); 2.75-2.64 (m, 2H); 2.74 (m, 2H); 2.34 (dd, J=7.8, 16.0 Hz, 1H); 2.30 (m, 2H); 1.94 (s, 3H); 1.67 (s, 3H); 1.41 (s, 3H); 1.17 (d, J=7.2 Hz, 3H); 1.10 (s, 3H); 1.01 (d, J=6.6 Hz, 3H); 0.93 (s, 9H); 0.90 (s, 9H), 0.86 (s, 9H); 0.23 (s, 3H); 0.14 (s, 3H); 0.06 (s, 3H); 0.01 (s, 6H); −0.01 (S, 3H).

Further elution was then performed (Hexane-Ethyl acetate 6-1) to give a second eluting isomer (0.4 g, 0.468 mmol) as an oil.

$^1$H NMR (300 MHz, CDCl3): 6.93 (s, 1H); 6.48 (s, 1H); 5.40-5.2 (m, 2H); 4.14-4.09 (m, 2H); 3.61 (dd, J=1.8, 8.4 Hz, 1H); 3.31 (dd, J=2.1, 16.5 Hz, 1H); 3.01 (qd, J=1.8, 7.2 Hz, 1H); 2.78 (m, 2H); 2.73 (s, 3H); 2.67 (m, 1H); 2.41 (dd, J=7.8; 16.5 Hz, 1H); 2.30 (m, 2H); 1.94 (s, 3H); 1.67 (s, 3H); 1.44 (s, 3H); 1.17 (d, J=7.2 Hz, 3H); 1.10 (s, 3H); 1.00 (d, J=6.6 Hz, 3H); 0.93 (s, 9H); 0.89 (s, 9H); 0.87 (s, 9H); 0.19 (s, 3H); 0.11 (s, 3H); 0.10 (s, 3H); 0.07 (s, 3H); 0.05 (s, 3H); 0.02 (s, 3H).

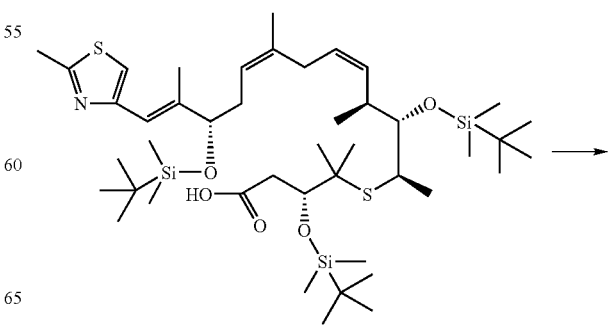

-continued

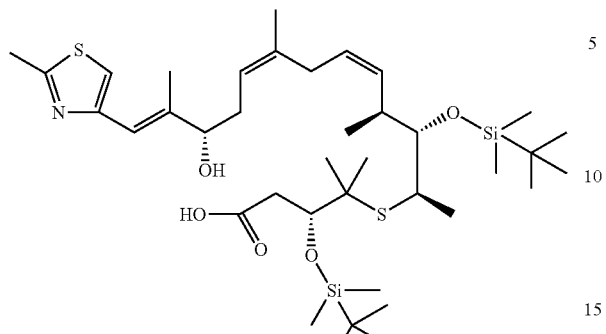

(3R)-3-(tert-Butyl-dimethyl-silanyloxy)-4-[(1'R,2'S, 3'S,4'Z,7'Z,10'S,11'E)-2'-(tert-butyl-dimethyl-silany-loxy)-10'-hydroxy-1',3',7',11'-tetramethyl-12'-(2-methyl-thiazol-4-yl)-dodeca-4',7',11'-trienylsulfanyl]-4-methyl-pentanoic acid To an ice cooled solution of substrate (0.2 g, 0.234 mmol) in tetrahydrofuran (5 mL) was added TBAF (2.2 mL, 1M in tetrahydrofuran, 2.2 mmol). The reaction was stirred 2 h at room temperature. The reaction mixture was diluted with 10% solution of NaHSO4 and extracted with ethyl acetate (5×50 mL). The combined organic layers were washed with brine and dried over sodium sulfate. After evaporation, the residue was chromatographed (dichloromethane-methanol 19-1) to afford the title compound (0.130 g, 0.1756 mmol) as a foam.

$^1$H NMR (300 MHz, CDCl3): 6.97 (s, 1H); 6.88 (s, 1H); 5.37-5.29 (m, 3H); 4.23 (dd, J=1.8, 8.1 Hz, 1H); 4.19 (dd, J=3.9, 9.4 Hz, 1H); 3.63 (d, J=8.4 Hz, 1H); 3.42 (dd, J=1.8, 16.2 Hz, 1H); 3.23-3.15 (m, 2H); 2.75 (m, 1H); 2.73 (s, 3H); 2.69 (m, 1H); 2.50-2.34 (m, 2H); 2.33 (dd, J=7.8, 15.9 Hz, 1H); 1.98 (s, 3H); 1.73 (s, 3H); 1.40 (s, 3H); 1.17 (d, J=7.2 Hz, 3H); 1.10 (s, 3H); 1.0 (d, J=6.6 Hz, 3H); 0.93 (s, 9H); 0.85 (s, 9H), 0.22 (s, 3H); 0.13 (s, 3H); 0.07 (s, 3H); −0.01 (s, 3H).

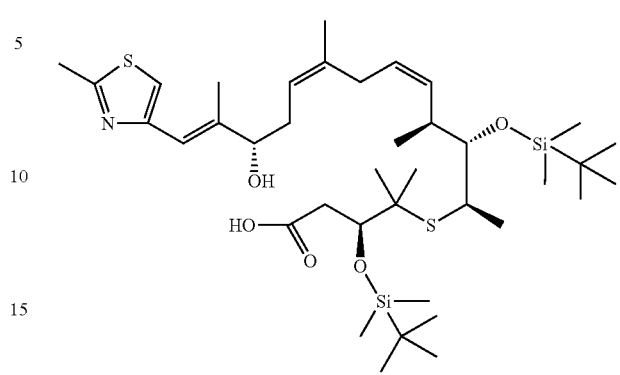

(3S)-3-(tert-Butyl-dimethyl-silanyloxy)-4-[(1R,2'S, 3'S,4'Z,7'Z,10'S,11'E)-2'-(tert-butyl-dimethyl-silany-loxy)-10'-hydroxy-1',3',7',11'-tetramethyl-12'-(2-methyl-thiazol-4-yl)-dodeca-4',7',11'-trienylsulfanyl]-4-mathyl-pentanoic acid To an ice cooled solution of substrate (0.2 g, 0.234 mmol) in tetrahydrofuran (5 ml) was added TBAF (2.2 mL, 1M in tetrahydrofuran, 2.2 mmol). The reaction was stirred 2 h at room temperature. The reaction mixture was diluted with 10% solution of NaHSO4 and extracted with ethyl acetate (5×50 mL). The combined organic layers were washed with brine and dried over sodium sulfate. After evaporation, the residue was chromatographed (DCM-MeOH 19-1) to afford the title compound (0.139 g, 0.1877 mmol) as a foam.

$^1$H NMR (300 MHz, CDCl3): 6.97 (s, 1H); 6.62 (s, 1H); 5.45-5.21 (m, 3H); 4.20-4.12 (m, 2H); 3.59 (dd, J=2.1, 7.8 Hz, 1H); 3.30 (dd, J=2.1, 16.8 Hz, 1H); 3.01 (qd, J=1.8, 7.2 Hz, 1H); 2.90-2.82 (m, 2H); 2.74 (s, 3H); 2.72 (m, 1H); 2.45-2.37 (m, 3H); 2.02 (s, 3H); 1.73 (s, 3H); 1.42 (s, 3H); 1.18 (d, J=7.2 Hz, 3H); 1.10 (s, 3H); 1.10 (d, J=6.6 Hz, 3H); 0.93 (s, 9H), 0.88 (s, 9H), 0.17 (s, 3H), 0.10 (s, 3H); 0.08 (S, 3H), 0.02 (s, 3H).

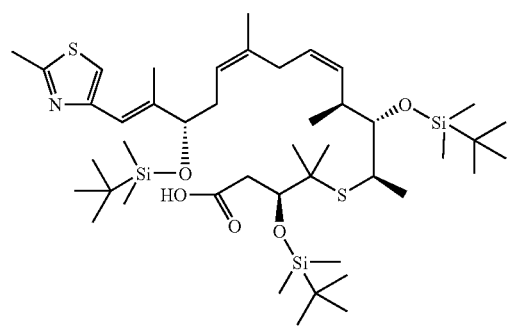

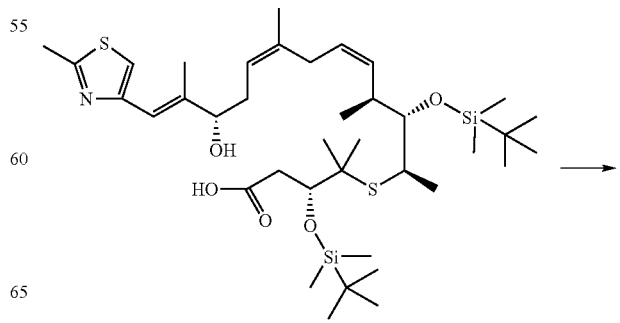

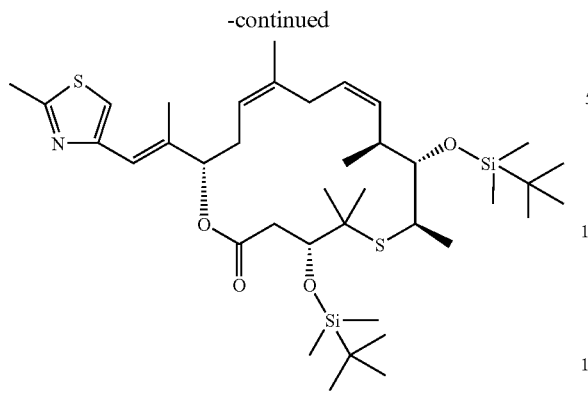

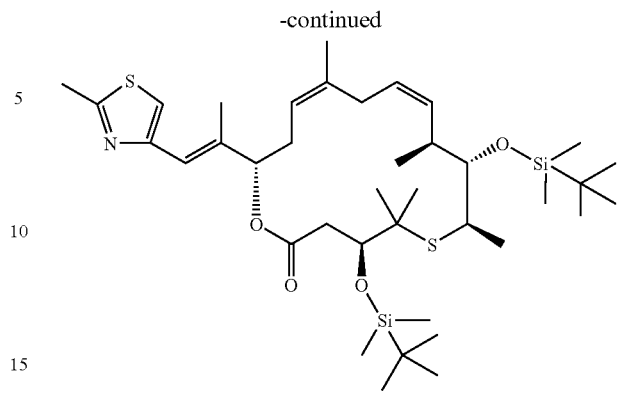

(4R,7R,8S,9S,10Z,13Z,16S)-4,8-Bis-(tert-butyl-dimethyl-silanyloxy)-5,5,7,9,13-pentamethyl-16-[(E)-1-methyl-2-(2-methyl-1,3-thiazol-4-yl)-ethenyl]-1-oxa-6-thia-cyclohexadeca-10,13-dien-2-one To an ice cooled solution of substrate (0.135 g, 0.18 mmol) in tetrahydrofuran (3 mL) was added triethylamine (0.151 mL, 1.08 mmol) and then 2,4,6-trichlorobenzoylchloride (0.067 mL, 0.428 mmol). The reaction was stirred at 0C for one hour. The reaction mixture was then added using a syringe pump to a solution of 4-DMAP (0.051 g, 0.416 mmol) in toluene (37 mL) at 70C over 2 h. After the addition was completed, the reaction was stirred 30 minutes at the same temperature. After cooling, the reaction mixture was evaporated to dryness. The residue was then filtered through a plug of silica gel (hexane-diethyl ether 1:1) to eliminate solids. The filtrate was concentrated in vacuo and the residue was purified by chromatography (hexane-ethyl acetate 19:1) to afford the title compound (0.093 g, 0.128 mmol) as a colorless oil.

$^1$H NMR (300 MHz, CDCl3): 6.91 (s, 1H); 6.40 (s, 1H); 5.45 (td, J=5.1, 11 Hz, 1H); 5.36 (t app, J=4.2 Hz, 1H); 5.31-5.23 (m, 2H); 4.20 (dd, J=2.4, 7.8 Hz, 1H); 3.67 (dd, J=2.7, 5.1 Hz, 1H); 3.33 (dd, J=9.6, 15.3 Hz, 1H); 3.12 (qd, J=2.7, 7.2 Hz, 1H); 2.91 (dd, J=7.8, 15.9 Hz, 1H); 2.81 (m, 1H); 2.72 (s, 3H); 2.58-2.49 (m, 3H); 2.46 (dd, J=2.7, 15.9 Hz, 1H); 2.16 (s, 3H); 1.77 (s, 3H); 1.39 (s, 3H); 1.21 (d, J=7.2 Hz, 3H); 1.19 (s, 3H); 1.00 (d, J=6.6 Hz, 3H); 0.93 (s, 9H); 0.91 (s, 9H), 0.09 (s, 3H), 0.06 (s, 3H); 0.03 (s, 3H); 0.01 (s, 3H).

(4S,7R,8S,9S,10Z,13Z,16S)-4,8-Bis-(tert-butyl-dimethylsilanyloxy)-5,5,7,9,13-pentamethyl-16-[(E)-1-methyl-2-(2-methyl-1,3-thiazol-4-yl)-ethenyl]-1-oxa-6-thia-cyclohexadeca-10,13-dien-2-one To an ice cooled solution of substrate (0.130 g, 0.18 mmol) in tetrahydrofuran (3 mL) was added triethylamine (0.151 mL, 1.08 mmol) and then 2,4,6-trichlorobenzoylchloride (0.067 mL, 0.428 mmol). The reaction was stirred at 0C. for one hour. The reaction mixture was then added using a syringe pump to a solution of 4-DMAP (0.051 g, 0.416 mmol) in toluene (37 mL) at 70° C. over 2 h. After the addition was completed, the reaction was stirred 30 minutes at the same temperature. After cooling, the reaction mixture was evaporated to dryness. The residue was then filtered through a plug of silica gel (hexane-diethyl ether 1:1) to eliminate solids. The filtrate was concentrated in vacuo and the residue was purified by chromatography (hexane-ehyl acetate 19:1) to afford the title compound (0.114 g, 0.128 mmol) as a colorless oil.

$^1$H NMR (300 MHz, CDCl3): 6.98 (s, 1H), 5.54 (s, 1H), 5.41-5.21 (m, 3H); 5.07 (t app, J=7.2 Hz, 1H); 4.30 (dd, J=3.6, 6.0 Hz, 1H); 3.33 (m, 2H); 2.99-2.77 (m, 4H); 2.73 (s, 3H); 2.53-2.37 (m, 3H); 2.11 (s, 3H), 1.77 (s, 3H), 1.44 (s, 3H), 1.36 (d, J=6.9 Hz, 3H); 1.14 (s, 3H); 1.00 (d, J=6.6 Hz, 3H), 0.93 (s, 9H), 0.87 (s, 9H), 0.15 (s, 3H); 0.07 (s, 3H), 0.04 (s, 3H), 0.03 (s, 3H).

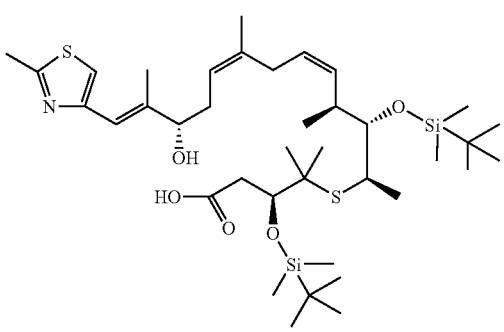

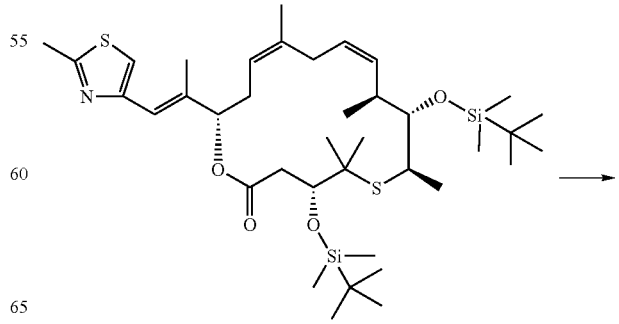

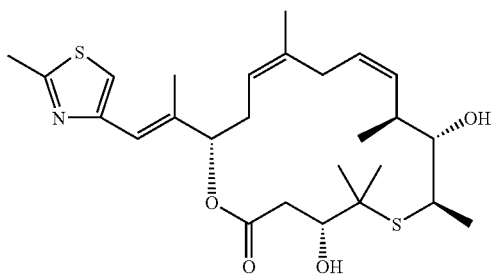

(4R,7R,8S,9S,10Z,13Z,16S)-4,8-Dihydroxy-5,5,7,9,
13-pentamethyl-16-[(E)-1-methyl-2-(2-methyl-1,3-
thiazol-4-yl)ethenyl]-1-oxa-6-thia-cyclohexadeca-10,
13-dien-2-one To an ice chilled solution of substrate (0.076 g, 0.105 mmol) in tetrahydrofuran (3 mL) were added a stock solution of HF-pyridine [7 mL, prepared by diluting HF.pyridine (4 mL) in a solution of pyridine (11.4 mL) in tetrahydrofuran (20 mL)) and HF.pyridine (1.8 mL)]. After stirring for 30 minutes at 0C, the solution was heated at 45C for 30 h. The reaction mixture was cooled down and the reaction was poured onto a saturated solution of NaHCO3 (50 mL). The pH was adjusted to 8 by adding solid sodium bicarbonate. The aqueous layer was extracted with ethyl acetate (4×50 mL) and the combined organic layers were washed with a saturated solution of copper sulfate (5×25 mL). The organic layer was then dried over sodium sulfate and concentrated in vacuo. The residue was chromatographed (hexane-ethyl acetate 1:1) to afford the title compound (0.048 g, 0.0972 mmol) as an oil.

MS (ESI, m/z): 494.5 [M+H+]$^1$H NMR (300 MHz, CDCl3):6.98 (s, 1H); 6.55 (s, 1H), 5.51-5.34 (m, 3H); 5.08 (m, 1H); 4.24 (m, 1H); 3.86 (br s, 1H); 3.49 (m, 1H); 3.33 (qd, J=4.2, 7.2 Hz, 1H); 3.06 (dd, J=6.0, 15.3 HZ, 1H); 2.93-2.74 (m, 5H); 2.73 (s, 3H); 2.61 (dd, J=5.4, 15.6 Hz, 1H); 2.41 (m, 1H); 2.12 (s,3H); 1.72 (s,3H); 1.51 (s, 3H); 1.36 (d, J=7.2 Hz, 3H); 1.27 (s, 3H); 1.07 (d, J=6.6 Hz, 3H).

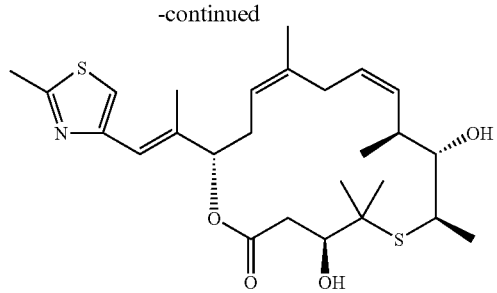

(4S,7R,8S,9S,10Z,13Z,16S)-4,8-Dihydroxy-5, 5, 7,
9, 13-pentamethyl-16-[(E)-1-methyl-2-(2-methyl-1,
3-thiazol-4-yl)ethenyl]-1-oxa-6-thia-cyclohexadeca-
10,13-dien-2-one To an ice chilled solution of substrate (0.04 g, 0.055 mmol) in tetrahydrofuran (3 mL) were added a stock solution of HF-pyridine [6 mL, prepared by diluting HF.pyridine (4 mL) in a solution of pyridine (11.4 mL) in tetrahydrofuran (20 mL)) and HF.pyridine (1 mL)]. After stirring for 30 minutes at 0C, the solution was heated at 45C for 30 h. The reaction mixture was cooled down and the reaction was poured onto a saturated solution of NaHCO3 (50 mL). The pH was adjusted to 8 by adding solid sodium bicarbonate. The aqueous layer was extracted with ethyl acetate (4×50 mL) and the combined organic layers were washed with a saturated solution of copper sulfate (5×25 mL). The organic layer was then dried over sodium sulfate and concentrated in vacuo. The residue was chromatographed (hexane-ethyl acetate 1:1) to afford the title compound (0.025 g, 0.0506 mmol) as an oil.

MS (ESI, m/z): 494.5 [M+H+]$^1$H NMR (300 MHz, CDCl3): 6.98 (s, 1H); 6.50 (s, 1H); 5.49-5.4 (m, 3H); 5.13 (t, J=7.8 Hz, 1H); 4.08 (m, 1H); 3.38 (m, 1H); 3.13-2.93 (m, 3H); 2.88 (dd, J=3.6 HZ, 1H); 2.81 (m, 1H); 2.72 (s, 3H), 2.66 (dd, J=3.3, 15.3 Hz, 1H); 2.54 (dd, J=5.1, 8.1 Hz, 1H); 2.46 (dd, J=8.4, 15.6 Hz, 1H); 2.10 (s, 3H); 2.0 (m, 1H); 1.74 (s, 3H); 1.43 (s, 3H); 1.38 (d, J=6.9 Hz, 3H); 1.28 (s, 3H); 1.08 (d, J=6.9 Hz, 3H).

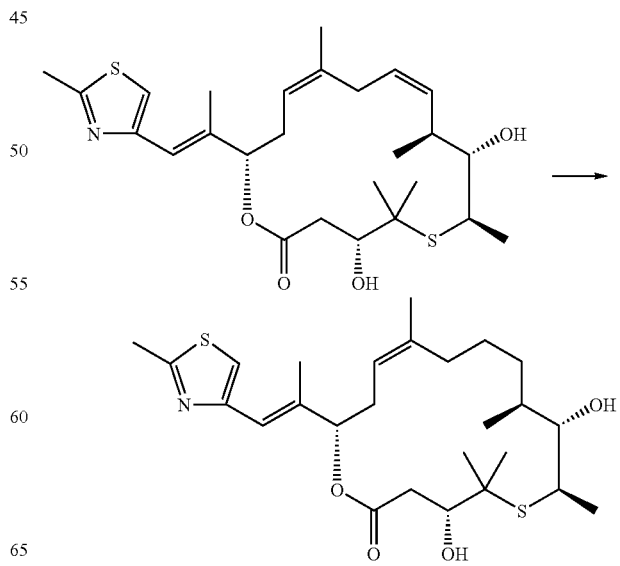

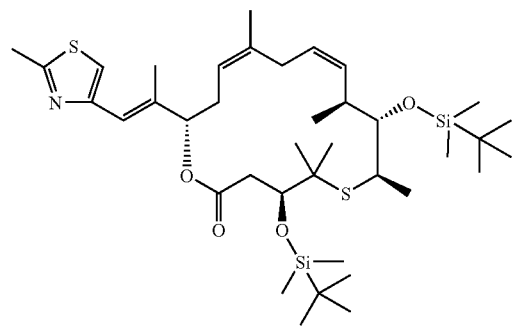

(4R,7R,8S,9S,10Z,13Z,16S)-4,8-Dihydroxy-5,5,7,9,13-pentamethyl-16-[(E)-1-methyl-2-(2-methyl-1,3-thiazol-4-yl)ethenyl]-1-oxa-6-thia-cyclohexadec-13-en-2-one To a solution of substrate (0.047 g, 0.095 mmol) in diethyl ether (3 mL) were added triethylamine (0.09 mL, 0.65 mmol) and triisopropylbenzenesulfonyl hydrazine (0.180 g, 0.6 mmol). The mixture was heated at 37C for 3 h. The reaction mixture was cooled and the solids were filtered off through a pad of silica gel using ether as an eluent. After concentration in vacuo, the residue was subjected to the reaction conditions previously described. This operation was repeated six times. After these cycles, the residue was purified by chromatography (hexane-ethyl acetate 1-2) to afford the title compound (0.030 g, 0.06 mmol) as an oil.

MS (ESI, m/z): 496.5[M+H$^+$]$^1$H NMR (300 MHz, CDCl3): 6.98 (s, 1H); 6.61 (s, 1H); 5.30 (dd, J=1.5, 7.2 Hz, 1H); 5.12 (m, 1H); 4.14 (dd, 1H); 3.55 (dd, J=1.8, 9.0 Hz, 1H); 3.39 (qd, J=1.8, 7.2 Hz, 1H); 2.80-2.60 (m, 3H); 2.72 (s, 3H); 2.4-2.35 (m, 2H); 2.33-2.20 (m, 2H); 2.08 (s, 3H); 1.92 (m, 1H); 1.69 (s, 3H); 1.58-1.42 (m, 4H); 1.42 (s, 3H); 1.30 (s, 3H); 1.22 (d, J=6.6 Hz, 3H); 1.06 (d, J=6.6 Hz, 3H).

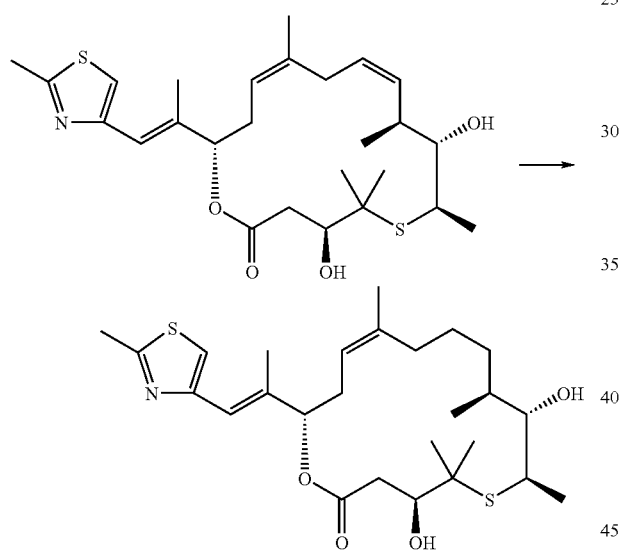

(4S,7R,8S,9S,10Z,13Z,16S)-4,8-Dihydroxy-5,5,7,9,13-pentamethyl-16-[(E)-1-methyl-2-(2-methyl-1,3-thiazol-4-yl)ethenyl]-1-oxa-6-thia-cyclohexadec-13-en-2-one To a solution of substrate (0.025 g, 0.0506 mmol) in diethyl ether (1.5 mL) were added triethylamine (0.044 mL, 0.32 mmol) and triisopropylbenzenesulfonyl hydrazine (0.088 g, 0.3 mmol). The mixture was heated at 37C for 3 h. The reaction mixture was cooled and the solids were filtered off through a pad of silica gel using ether as an eluent. After concentration in vacuo, the residue was subjected to the reaction conditions previously described. This operation was repeated six times. After these cycles, the residue was purified by chromatography (hexane-ethyl acetate 1-2) to afford the title compound (0.015 g, 0.030 mmol) as an oil.

MS (ESI, m/z): 496.4[M+H$^+$]$^1$H NMR (300 MHz, CDCl3): 6.98 (s, 1H); 6.50 (s, 1H); 5.42 (dd, J=2.9, 7.2 Hz, 1H); 5.16 (t, J=6.9 HZ, 1H); 4.02 (td, J=1.5, 9.7 Hz, 1H); 3.50 (m, 1H); 3.18 (qd, J=2.4, 7.0 HZ, 1H); 3.11 (d, J=2.5 HZ, 1H); 2.89 (dd, J=2.5, 14.8 HZ, 1H); 2.72 (s, 3H); 2.56-2.46 (m, 2H); 2.41 (dd, J=10, 14.9 Hz, 1H); 2.12-1.95 (m, 3H); 2.08 (S, 3H); 1.69 (s, 3H); 1.62 (br s, 1H); 1.46-1.20 (m, 4H); 1.38 (s, 3H); 1.32 (s, 3H); 1.27 (d, J=6.6 HZ, 3H); 1.05 (d, J=6.6 HZ, 3H).

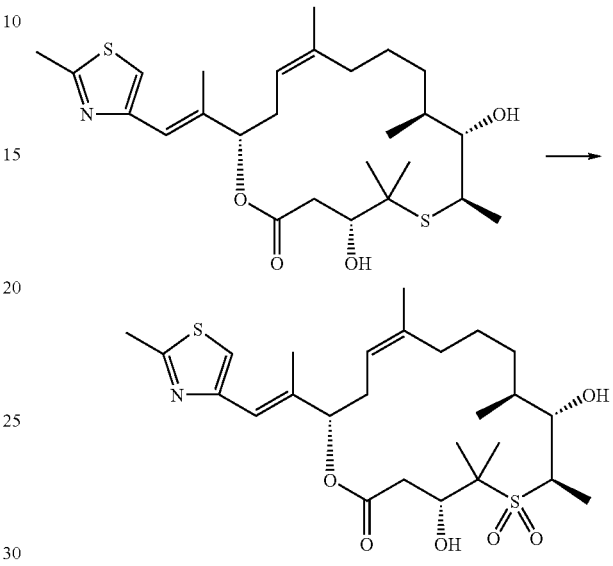

(4R,7R,8S,9S,10Z,13Z,16S)-4,8-Dihydroxy-5,5,7,9,13-pentamethyl-16-[(E)-1-methyl-2-(2-methyl-1,3-thiazol-4-yl)-ethenyl]-6,6-dioxo-1-oxa-6$\lambda^6$-thia-cyclohexadec-13-en-2-one To a solution of substrate (0.005 g, 0.01 mmol) in dichloromethane (0.3 mL) was added at −78C, 3-chloroperoxybenzoic acid (0.0042 g, 0.024 mmol). The reaction mixture was then stirred at the same temperature for 20 minutes. The reaction mixture was directly chromatographed (hexane-ethyl acetate 1-3) to afford the title compound (0.0032 g, 0.006 mmol) as an oil.

MS (ESI, m/z): 528.0 [M+H$^+$]$^1$H NMR (300 MHz, CDCl3): 6.99 (s, 1H); 6.75 (s, 1H); 5.49 (dd, J=1.5, 10.2 Hz, 1H); 5.13 (m, 1H); 4.31-4.15 (m, 2H); 3.96 (m, 1H); 3.38 (br s, 1H); 2.92-2.70 (m, 2H); 2.73 (s, 3H); 2.59 (m, 1H); 2.4 (m, 1H); 2.35-1.92 (m, 4H); 2.11 (s, 3H); 1.66 (s, 3H), 1.65-1.3 (m, 4H); 1.56 (s, 3H) 1.43-1.40 (s and d overlapped, 6H); 1.12 (d, J=6.6 Hz, 3H).

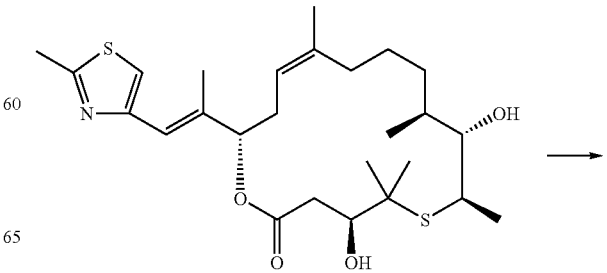

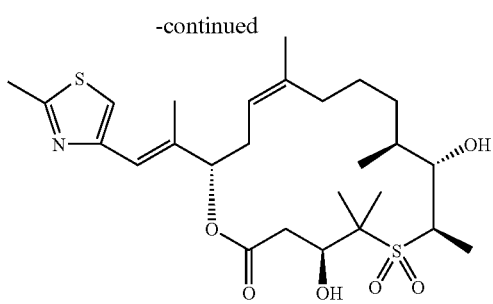

(4S,7R,8S,9S,10Z,13Z,16S)-4,8-Dihydroxy-5,5,7,9,
13-pentamethyl-16-[(E)-1-methyl-2-(2-methyl-1,3-
thiazol-4-yl)ethenyl]-6,6-dioxo-1-oxa-6λ⁶-thia-cy-
clohexadec-13-en-2-one To a solution of substrate (0.005 g, 0.01 mmol) in dichloromethane (0.3 mL) was added at −78C, 3-chloroperoxybenzoic acid 0.0042 g, 0.024 mmol). The reaction mixture was then stirred at the same temperature for 20 minutes. The reaction mi(ture was directly chromatographed (hexane-ethyl acetate 1-3) to afford the title compound (0.0030 g, 0.0056 mmol) as an oil.

MS (ESI, m/z): 528.0 [M+H⁺]¹H NMR (300 MHz, CDCl3): 6.99 (s, 1H); 6.55 (s, 1H); 5.49 (dd, J=2.3, 9.6 Hz, 1H); 5.13 (m, 1H); 4.50 (td, J=2.8, 10.8 Hz, 1H); 4.22 (d, J=9.5 Hz, 1H); 4.05 (q, J=7.5 HZ, 1H); 3.38 (br s, 1H); 2.78-2.72 (m, 1H); 2.65-2.49 (m, 2H), 2.42 (br s, 1H); 2.36-2.28 (m, 2H); 2.11 (s, 3H), 2.10 (m, 1H); 1.90 (m, 1H); 1.70 (s, 3H); 1.58-1.30 (m, 4H); 1.46-1.42 (s and d overlapped, 6H); 1.37 (s, 3H); 1.09 (d, J=6.6 Hz, 3H).

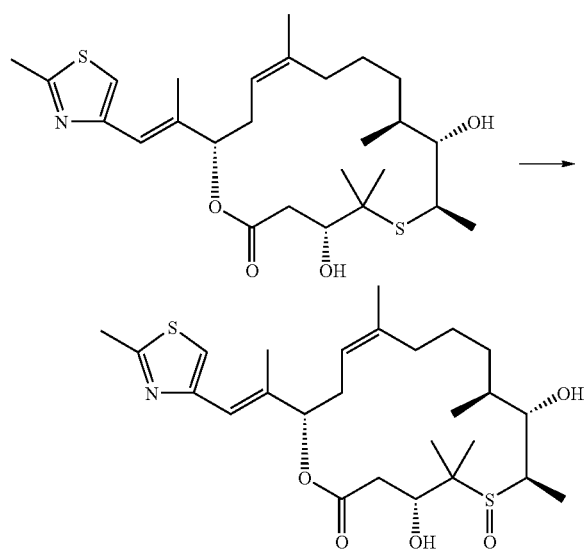

(4R,7R,8S,9S,10Z,13Z, 16S)-4,8-Dihydroxy-5,5,7,9,
13-pentamethyl-16-[(Z)-1-methyl-2-(2-methyl-1,3-
thiazol-4-yl)ethenyl]-6-oxo-1-oxa-6λ⁶-thia-cyclo-
hexadec-13-en-2-one To a solution of substrate (0.009 g, 0.0181 mmol) in dichloromethane (0.5 mL) was added at −78C, 3-chloroperoxybenzoic acid (0.0037 g, 0.022 mmol). The reaction was stirred at the same temperature for 10 minutes and 10% sodium metabisulfite (0.1 mL) was added. After warming up to room temperature, the mixture was directly purified by chromatography (hexane-ethyl acetate 1-2) to afford the title compound (0.0034 g, 0.0066 mmol) as an oil MS (ESI, m/z): 512.5[M+H⁺]¹H NMR (300 MHz, CDCl3): 6.96 (s, 1H); 6.55 (s, 1H); 5.29 (dd, J=2.4, 9.5 Hz, 1H); 5.16 (m, 1H); 5.00 (br s, 1H); 4.83 (t, J=6.9 HZ, 1H), 4.1 (d, J=9.3 HZ, 1H); 3.50 (m, 1H); 3.00 (br s, 1H); 2.73 (s, 3H); 2.73-2.51 (m, 2H); 2.43-2.20 (m, 3H); 2.10 (s, 3H); 1.96 (m, 1H); (m, 1H); 1.66 (s, 6H); 1.61 (d, 3H), 1.60-1.3 (m, 4H); 1.42 (d, J=7.2 Hz, 3H), 1.15 (d, J=6.3 HZ, 3H); 1.07 (s, 3H).

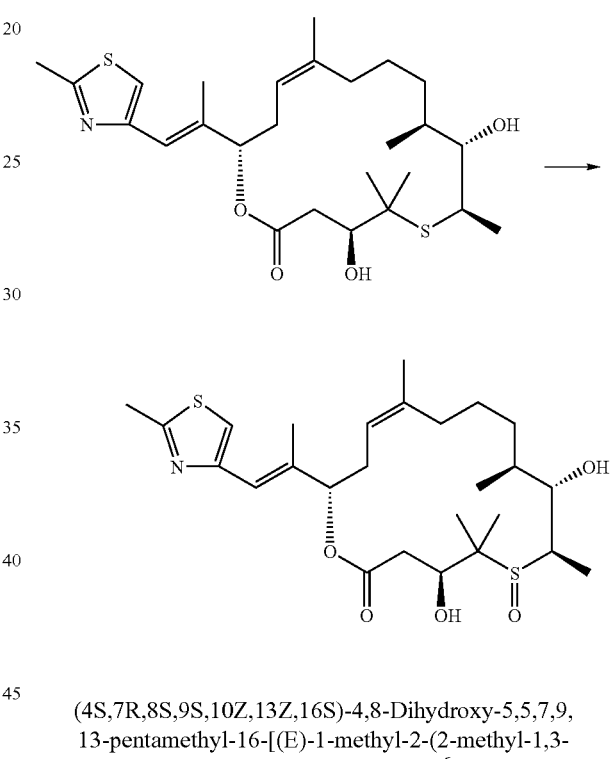

(4S,7R,8S,9S,10Z,13Z,16S)-4,8-Dihydroxy-5,5,7,9,
13-pentamethyl-16-[(E)-1-methyl-2-(2-methyl-1,3-
thiazol-4-yl)ethenyl]-6-oxo-1-oxa-6λ⁶-thia-cyclo-
hexadec-13-en-2-one To a solution of substrate (0.005 g, 0.01 mmol) in dichloromethane (0.5 mL) was added at −78C, 3-chloroperoxybenzoic acid (0.0024 g, 0.012 mmol). The reaction was stirred at the same temperature for 10 minutes and 10% sodium metabisulfite (0.1 mL) was added. After warming up to room temperature, the mixture was directly purified by chromatography (hexane-ethyl acetate 1-2) to afford the title compound (0.0021 g, 0.0041 mmol) as an oil MS (ESI, m/z): 496.5[M+H⁺]¹H NMR (300 MHz, CDCl3): 6.99 (s, 1H); 6.57 (s, 1H); 5.50 (m, 1H); 5.12 (m, 1H); 4.31 (d, J=10.2 HZ, 1H); 4.06 (d, J=9.9 Hz, 1H); 3.58 (q, J=7.4 Hz, 1H); 3.33 (br s, 1H); 3.20 (br s, 1H); 2.79 (d, J=15.4 Hz, 1H); 2.73 (s, 3H); 2.62-2.43 (m, 3H); 2.19-1.94 (m, 3H); 2.10 (s, 3H); 1.66 (s, 3H); 1.50-1.35 (m, 4H); 1.43 (d, J=7.2 HZ, 3H); 1,37 (s, 3H); 1.33 (s, 3H); 1.06 (d, J=6.6 HZ, 3H).

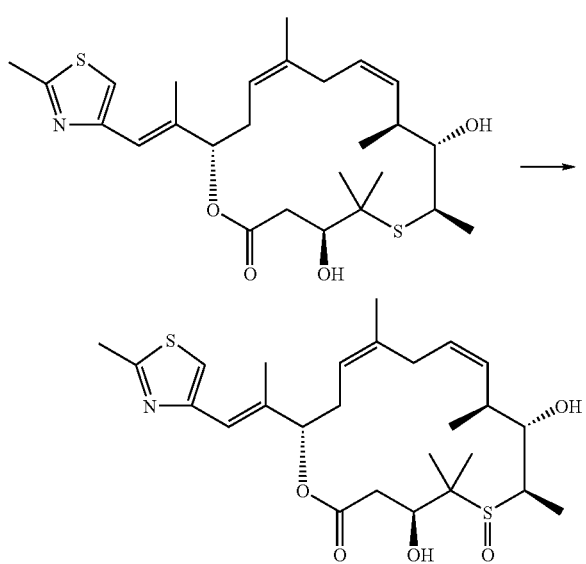

(4S,7R,8S,9S,10Z,13Z,16S)-4,8-Dihydroxy-5,5,7,9,
13-pentamethyl-16-[(E)-1-methyl-2-(2-methyl-1,3-
thiazol-4-yl)ethenyl]-6-oxo-1-oxa-6λ$^6$-thia cyclo-
hexadec-10,13-dien-2-one To a solution of substrate (0.010 g, 0.02 mmol) in dichloromethane (0.5 mL) was added at −78C, 3-chloroperoxybenzoic acid (0.0024 g, 0.012 mmol). The reaction was stirred at the same temperature for 10 minutes and 10% sodium metabisulfite (0.1 mL) was added. After warming up to room temperature, the mixture was directly purified by chromatography (hexane-ethyl acetate 1-2) to afford the title compound (0.009 g, 0.0017 mmol) as an oil.

MS (ESI, m/z): 510.5 [M+H$^+$]$^1$H NMR (300 MHz, CDCl3): 6.99 (s, 0.66H); 6.98 (s, 0.33H); 6.54 (s, 066H); 6.44 (s, 0.33H); 5.70 (td, J=8.3, 10.7 Hz, 0.66H); 5.6 (m, 0.33H); 5.48 (dd, J=2.8, 9.3 Hz, 0.66H); 5.4 (t, J=4.9 Hz, 0.33H); 5.20-5.11 (m, 1.33H); 5.53 (dd, J=3, 8.7 Hz, 0.33H); 4.34 (br d, J=10.5 Hz, 0.66H); 4.06 (d, J=9.4 Hz, 0.66H); 3.61 (m, 0.33H); 3.50 (m, 0.66H); 3.36 (q, J=7.2 Hz, 0.66H); 2.93 (m, 0.33H); 2.86-2.41 (m, H); 2.11 (s, 1.98H); 1.02 (s, 1.02H); 1.76 (s, 1.98H); 1.74 (s, 1.02H); 1.50 (d, J=7.3 Hz, 1.98H); 1.47 (s, 1.02H); 1.38 (d, J=7.3 Hz, 1.02H); 1.29 (s, 1.98H); 1.21 (s, 1.02H); 1.19 (s, 1.98H); 1.07-1.03 (two overlapped d, 3H).

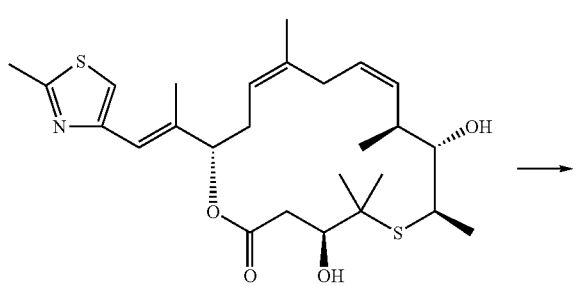

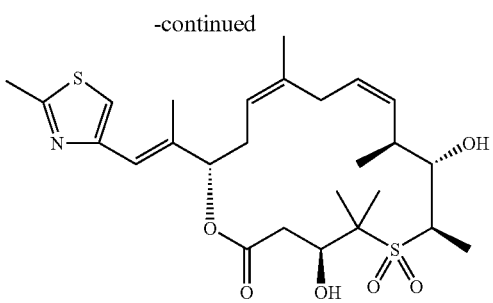

(4S,7R,8S,9S,10Z,13Z,16S)-4,8-Dihydroxy-5,5,7,9,
13-pentamethyl-16-[(E)-1-methyl-2-(2-methyl-1,3-
thiazol-4-yl)ethenyl]-6,6-dioxo-1-oxa-6λ$^6$-thia-cy-
clohexadeca-10,13-dien-2-one To a solution of substrate (0.008 g, 0.016 mmol) in dichloromethane (0.5 mL) was added at −78C, 3-chloroperoxybenzoic acid (0.0024 g, 0.012 mmol). The reaction was stirred at the same temperature for 10 minutes and 10% sodium metabisulfite (0.1 mL) was added. After warming up to room temperature, the mixture was directly purified by chromatography (hexane-ethyl acetate 1-4) to afford the title compound (0.0029 g, 0.0055 mmol) as an oil MS (ESI, m/z):526.3 [M+H$^+$]$^1$H NMR (300 MHz, CDCl3): 6.99 (s, 1H); 6.50 (s, 1H); 5.72 (m, 1H); 5.46-5.31 (m, 2H); 5.16 (m, 1H); 4.40 (m, 1H); 4.23 (m, 1H); 3.77 (q, J=7.2 Hz, 1H); 3.62 (d, J=2.3 Hz, 1H); 2.71-2.54 (m, 4H); 2.73 (s, 3H); 2.48-2.38 (m, 2H); 2.30 (d, J=3.6 Hz, 1H); 2.11 (s, 3H); 1.73 (s, 3H); 1.50 (d, J=7.2 Hz, 3H); 1.43 (s, 3H); 1.37 (s, 3H); 1.08 (d, J=6.6 Hz, 3H).

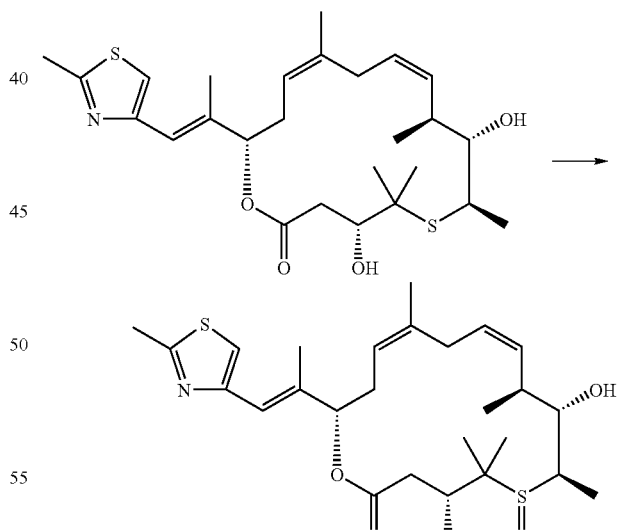

(4R,7R,8S,9S,10Z,13Z,16S)-4,8-Dihydroxy-5,5,7,9,
13-pentamethyl-16-[(E)-1-methyl-2-(2-methyl-1,3-
thiazol-4-yl)ethenyl]-6-oxo-1-oxa-6λ$^6$-thia cyclo-
hexadec-10,13-dien-2-one To a solution of substrate (0.0103 g, 0.0211 mmol) in dichloromethane (0.45 mL) was added 3-chloroperoxybenzoic acid (0.004 g, 0.022 mmol) at −78° C. The mixture was stirred at −78C for 10 minutes and was diluted with ethyl acetate (0.45 mL). The mixture was directly subjected to chromatography (hexane-ethyl acetate 1:4 then 0:1) to afford the title compound (0.0084 g, 0.016 mmol) as an oil MS (ESI, m/z):510.5 [M+H$^+$]$^1$H NMR (300 MHz, CDCl3): 6.96 (s, 1H); 6.48 (s, 1H); 5.74 (td, J=7, 11.1 Hz, 1H); 5.42 (t, J=10.3 Hz, 1H); 5.28 (dd, J=2.9, 8.3 HZ, 1H); 5.18-5.12 (m, 2H); 4.84 (t, J=7.2 Hz, 1H); 4.22 (br d, J=8.3 Hz, 1H); 3.44 (q, J=7.2 Hz, 1H); 2.93 (dd, J=7.9, 15.4 Hz, 1H); 2.79 (dd, J=6.3, 15.4 Hz, 1H); 2.72 (s, 3H); 2.72-2.51 (m, 5H); 2.39 (m, 1H); 2.18 (s, 3H); 1.76 (s, 3H); 1.59 (s, 3H); 1.48 (d, J=7.2 Hz, 3H); 1.17 (d, J=6.5 Hz, 3H); 1.01 (s, 3H).

(4R,7R,8S,9S,10Z,13Z,16S)-4,8-Dihydroxy-5,5,7,9, 13-pentamethyl-16-[(E)-1-methyl-2-(2-methyl-1,3-thiazol-4-yl)ethenyl]-6,6-dioxo-1-oxa-6λ$^6$-thia-cy-clohexadeca-10,13-dien-2-one To a solution of substrate (0.008 g, 0.016 mmol) in dichloromethane (0.5 mL) was added at −78° C., 3-chloroperoxybenzoic acid (0.0024 g, 0.012 mmol). The reaction was stirred at the same temperature for 10 minutes and 10% sodium metabisulfite (0.1 mL) was added. After warming up to room temperature, the mixture was directly purified by chromatography (hexane-ethyl acetate 1-4) to afford the title compound (0.0029 g, 0.0055 mmol) as an oil MS (ESI, m/z):526.3 [M+H$^+$]$^1$H NMR (300 MHz, CDCl3): 6.98 (s, 1H); 6.54 (s, 1H); 5.73 (td, J=9.0, 9.6 Hz, 1H); 5.52 (dd, J=2.6, 9.6 Hz, 1H); 5.34 (t, J=10.6 Hz, 1H); 5.10 (dd, J=5.1, 10.2 Hz, 1H); 4.42 (d, J=8.7 Hz, 1H); 4.13 (dd, J=3.5, 10.2 Hz, 1H); 3.67 (q, J=6.8 Hz, 1H); 3.41 (br s, 1H); 3.00 (dd, J=10.6, 16.7 Hz, 1H); 2.82-2.56 (m, 5H), 2.72 (s, 3H); 2.33 (m, 1H); 2.11 (s, 3H); 2.08 (br s, 1H); 1.70 (s, 3H); 1.56 (s, 3H); 1.50 (d, J=6.9 Hz, 3H); 1.36 (s, 3H); 1.11 (d, J=6.5 Hz, 3H).

The corresponding epoxides of all 5-thioepothilone derivatives are obtained by known procedures (Nicolaou et al. Angew. Chem. Int. Ed. 1998, 37, 2014-2045).

An alternative approach to synthesize the compounds of the present invention herein follows the route described in WO0232844. In these schemes, the groups p$^1$, p$^2$ and p$^3$ independently represent hydrogen or protecting groups, such as Acetyl or TBDMS)

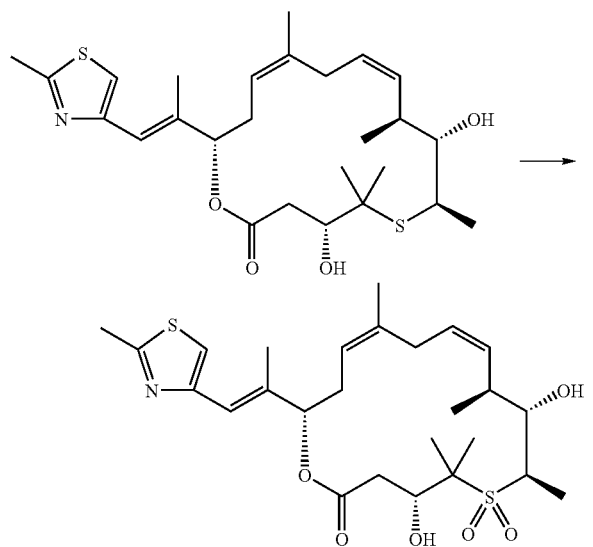

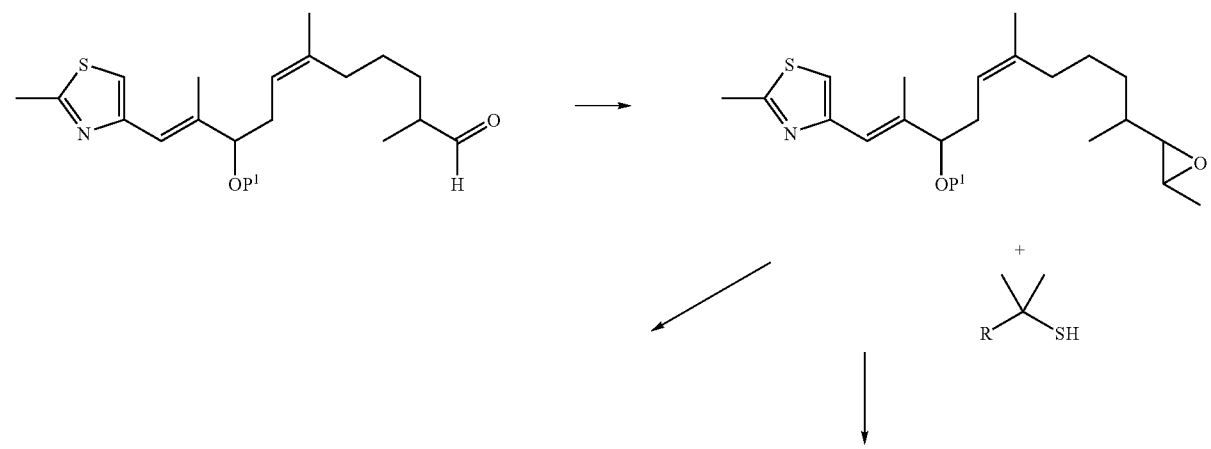

43                                              44
-continued
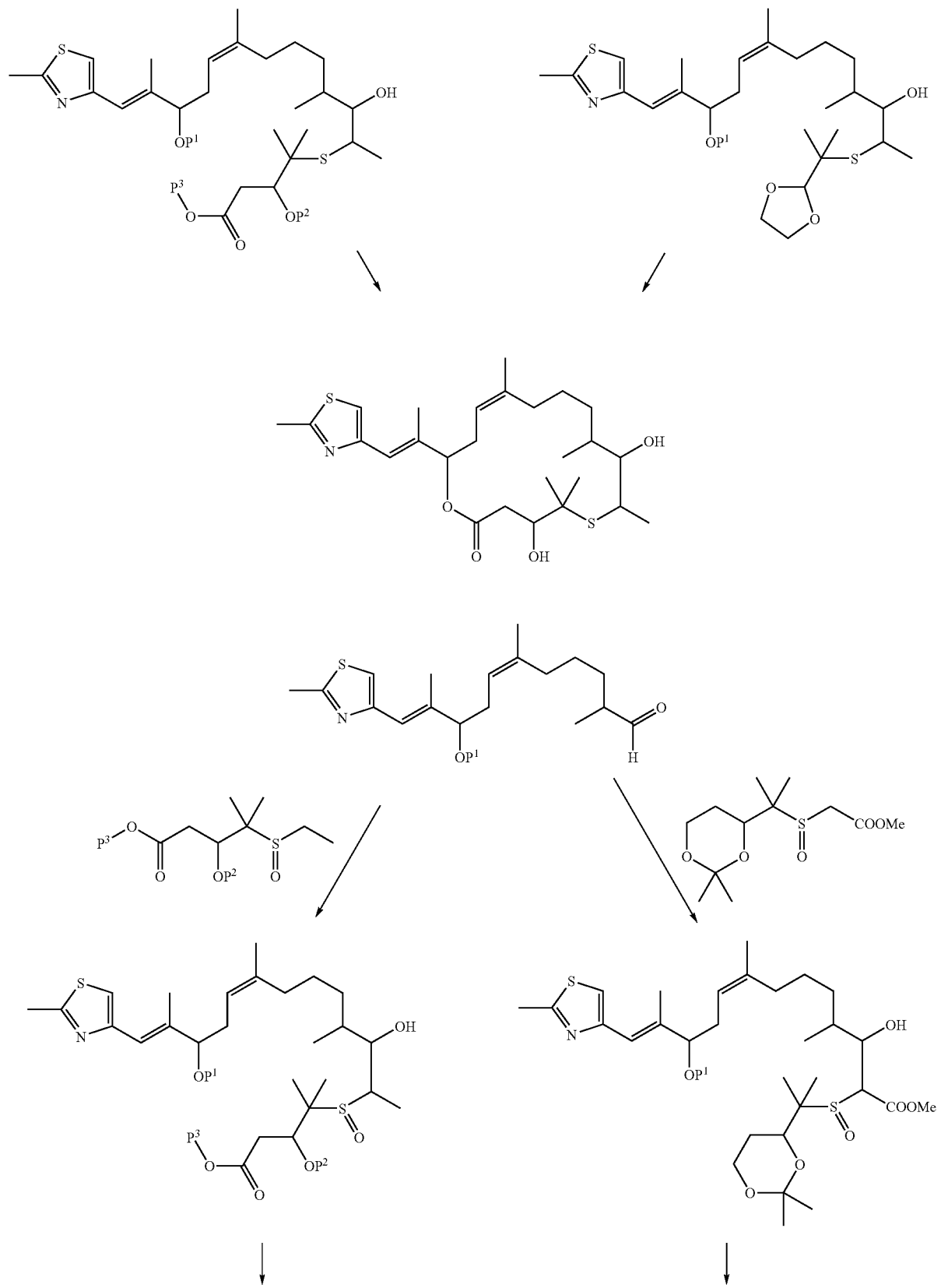

-continued

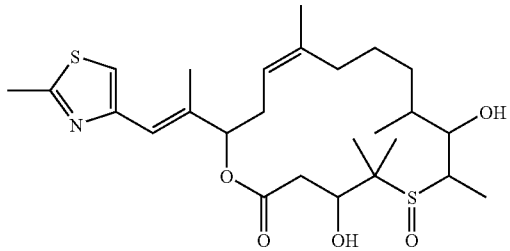
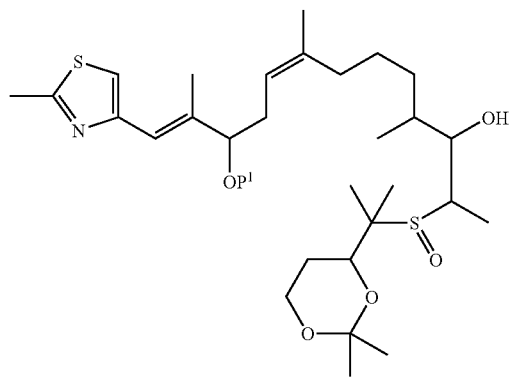

The invention claimed is:
1. A compound of Formula (I)

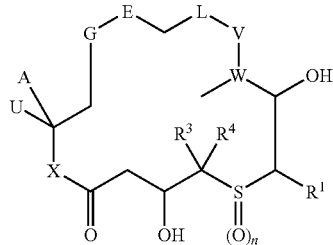

wherein
A is a group of formula (II):

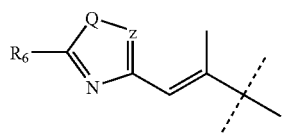

wherein Q is sulphur or oxygen, z is CH, and $R^6$ is $CH_3$, $CH_2OH$ or $CH_2NH_2$,
U is hydrogen,
G-E is selected from the following groups,

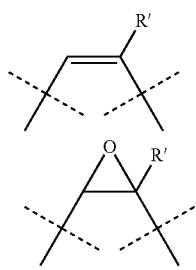
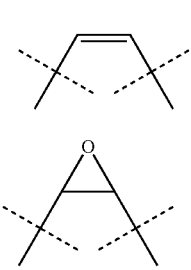

wherein R' is methyl,
$R^1$ is $C_1$-$C_4$-alkyl-,
L-V-W is a group of formula CH=CH—CH, $CH_2$—$CH_2$—CH or $CH_2$—CH=C, wherein the double bonds may be cis or trans isomers,
n is 0 or 2,
X is oxygen or NH; and
$R^3$ and $R^4$ are each methyl,
or a pharmacologically acceptable salt thereof.

2. A method for treating a patient suffering from or susceptible to breast cancer or epidermoid cancer, comprising administering to the patient a compound of claim 1.

3. The method of claim 2 wherein the patient is identified as suffering from breast cancer or epidermoid cancer and selected for treatment for breast cancer or epidermoid cancer, and the compound is administered to the identified and selected patient.

4. A compound of claim 1, wherein X is oxygen or NH.

5. A compound of claim 1, wherein $R^1$ is methyl, ethyl or propyl.

6. A compound of claim 1, wherein $R^3$ and $R^4$ are methyl groups.

7. A compound of claim 1 wherein A is

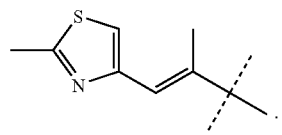

8. A pharmaceutical composition comprising a compound of claim 1 or a pharmacologically acceptable salt-thereof.

9. The pharmaceutical composition of claim 8, further comprising one or more carriers, adjuvants, diluents or mixtures thereof.

10. A method for treating a patient suffering from or susceptible to ovarian cancer, lung cancer, prostate cancer, cervix carcinoma, cancer of the bladder or leukemia, comprising administering to the patient a compound of claim 1.

* * * * *